US008257965B2

(12) United States Patent
Fang et al.

(10) Patent No.: US 8,257,965 B2
(45) Date of Patent: *Sep. 4, 2012

(54) ARRAYS OF BIOLOGICAL MEMBRANES AND METHODS AND USE THEREOF

(75) Inventors: Ye Fang, Painted Post, NY (US); Anthony G. Frutos, Painted Post, NY (US); Steven J. Jonas, Bloomfield Hills, MI (US); Peter J. Kalal, Corning, NY (US); Joydeep Lahiri, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/696,622

(22) Filed: Jan. 29, 2010

(65) Prior Publication Data

US 2010/0184626 A1     Jul. 22, 2010

Related U.S. Application Data

(63) Continuation of application No. 09/974,415, filed on Oct. 9, 2001, now Pat. No. 7,678,539, which is a continuation-in-part of application No. 09/854,786, filed on May 14, 2001, now Pat. No. 6,977,155.

(51) Int. Cl.
*C12M 1/34* (2006.01)
(52) U.S. Cl. ............................ 435/287.1; 435/4; 435/7.2
(58) Field of Classification Search ........................ None
See application file for complete search history.

(56) References Cited

U.S. PATENT DOCUMENTS

| | | | |
|---|---|---|---|
| 4,802,951 A | 2/1989 | Clark et al. | |
| 4,933,285 A | 6/1990 | Patton | |
| 5,677,196 A | 10/1997 | Herron et al. | |
| 5,756,355 A | 5/1998 | Lang et al. | |
| 5,759,774 A | 6/1998 | Hackett et al. | |
| 5,919,576 A | 7/1999 | Hui et al. | |
| 6,117,990 A | 9/2000 | Bonini et al. | |
| 6,228,326 B1 | 5/2001 | Boxer et al. | |
| 6,383,778 B1 | 5/2002 | Zuker et al. | |
| 6,451,543 B1 | 9/2002 | Kochendoerfer et al. | |
| 6,503,452 B1* | 1/2003 | Boxer et al. | 506/23 |
| 6,977,155 B2* | 12/2005 | Lahiri et al. | 435/7.2 |
| 7,160,687 B1* | 1/2007 | Kapur et al. | 435/7.2 |
| 7,678,539 B2* | 3/2010 | Fang et al. | 435/4 |
| 7,858,375 B2* | 12/2010 | Zhu et al. | 436/71 |
| 2002/0019015 A1 | 2/2002 | Lahiri et al. | |
| 2005/0123563 A1* | 6/2005 | Doranz et al. | 424/204.1 |
| 2008/0207466 A1* | 8/2008 | Mozdy et al. | 506/12 |
| 2009/0239761 A1* | 9/2009 | Blackburn et al. | 506/9 |

FOREIGN PATENT DOCUMENTS

| | | |
|---|---|---|
| WO | WO 96/26432 | 8/1996 |
| WO | WO 98/16830 | 4/1998 |
| WO | WO 98/23948 | 6/1998 |
| WO | WO 99/35289 | 7/1999 |
| WO | WO 00/04389 | 1/2000 |
| WO | WO 00/32044 | 6/2000 |
| WO | WO 01/01142 | 1/2001 |
| WO | WO 01/20330 | 3/2001 |
| WO | WO 01/26800 | 4/2001 |
| WO | WO 01/88182 | 11/2001 |
| WO | WO 01/98747 A2 | 12/2001 |

OTHER PUBLICATIONS

Bieri, "Micropatterned immobilization of a G protein-coupled receptor and direct detection of G protein activation",, Nature Biotechnology, vol. 17, Nov. 1999, pp. 1105-1108.*
Paul S. Cremer et al., "Creating Spatially Addressed Arrays of Planar Supported Fluid Phospholipid Membranes", J. Am. Chem. Soc. 1999, vol. 121, No. 35, pp. 8130-8131.
Paul S. Cremer et al., "Formation and Spreading of Lipid Bilayers on Planar Glass Supports", J. Phys. Chem. B, 1999, vol. 103, No. 13, pp. 2554-2559.
Christoph Bieri et al., "Micropatterned Immobilization of a G Protein-Coupled Receptor and Direct Detection of G Protein Activation", Nature Biotechnology, vol. 17, Nov. 1999, pp. 1105-1108.
Jennifer S. Hovis et al., "Patterning Barriers to Lateral Diffusion in Supported Lipid Bilayer Membranes by Blotting and Stamping", Langmuir, vol. 16, No. 3, 2000, pp. 894-897.
A.L. Plant, "Supported Hybrid Bilayer Membranes as Rugged Cell Membrane Mimics", Langmuir 1999, vol. 15, pp. 5128-5135.
H. Lang et al., "A New Class of Thiolipids for the Attachment of Lipid Bilayers on Gold Surfaces", Langmuir 1994, vol. 10, pp. 197-210.
B. Raguse et al., "Tethered Lipid Bilayer Membranes: Formation and Ionic Reservoir Characterization", Langmuir 1998, vol. 14, pp. 648-659.
A.Q. Emili et al., "Large-scale functional analysis using peptide or protein arrays", Nature Biotechnology, vol. 18, Apr. 2000, pp. 393-397.
J.T. Groves et al., "Micropatterning Fluid Lipid Bilayers on Solid Supports", Science, vol. 275, Jan. 31, 1997, pp. 651-653.
J.T. Groves et al., "Substrate-Membrane Interactions : Mechanisms for Imposing Patterns on a Fluid Bilayer Membrame", Langmuir, 1998, vol. 14, pp. 3347-3350.
J.M. Stadel et al., "Orphan G Protein-Coupled Receptors: A Neglected Opportunity for Pioneer Drug Discovery", TiPS, Nov. 1997, vol. 18, pp. 430-437.
G. MacBeath et al., "Printing Proteins as Microarrays for High-Throughput Function Determination", Science, Sep. 8, 2000, vol. 289, pp. 1760-1763.
J. Drews, "Drug Discovery: A Historical Perspective", Science, Mar. 17, 2000, vol. 287, pp. 1960-1964.
A.D. Howard et al., "Orphan G-Protein-Coupled Receptors and Natural Ligand Discovery", Trends in Pharmacological Sciences, Mar. 2001, vol. 22, No. 3, pp. 132-140.
O. Civelli et al., "Orphan Receptors, Novel Neuropeptides and Reverse Pharmaceutical Research", Brain Research 848, 1999, pp. 63-65.

(Continued)

*Primary Examiner* — Ann Lam
(74) *Attorney, Agent, or Firm* — John L. Haack

(57) ABSTRACT

The present invention overcomes the problems and disadvantages associated with prior art arrays by providing an array comprising a plurality of biological membrane microspots associated with a surface of a substrate that can be produced, used and stored, not in an aqueous environment, but in an environment exposed to air under ambient or controlled humidities. Preferably, the biological membrane microspots comprise a membrane bound protein. Most preferably, the membrane bound protein is a G-protein coupled receptor, an ion channel, a receptor serine/threonine kinase or a receptor tyrosine kinase.

9 Claims, 16 Drawing Sheets

OTHER PUBLICATIONS

V.V. Gurevich et al., "Agonist-Receptor-Arrestin, an Alternative Ternary Complex with High Agonist Affinity", The Journal of Biological Chemistry, Nov. 14, 1997, vol. 272, No. 46, pp. 28849-28852.

R.H. Oakley et al., "Differential Affinities of Visual Arrestin, βArrestin1, and βArrestin1 for G Protein-Coupled Receptors Delineate Two Major Classes of Receptors", The Journal of Biological Chemistry, Jun. 2, 2000, vol. 275, No. 22, pp. 17201-17210.

L.S. Barak et al., "A β-Arrestin/Green Fluorescent Protein Biosensor for Detecting G Protein-Coupled Receptor Activation", The Journal of Biological Chemistry, Oct. 31, 1997, vol. 272, No. 44, pp. 27497-27500.

A. Kovoor et al., "Targeted Construction of Phosphorylation-Independent β-Arrestin Mutants with Constitutive Activity in Cells", The Journal of Biological Chemistry, Mar. 12, 1999, vol. 274, No. 11, pp. 6831-6834.

J. Lahiri et al., "Method for Fabricating Supported Bilayer Lipid Membranes on Gold", Langmuir, 2000, vol. 16, pp. 7805-7810.

W.W. Shen et al., "Polymer-Supported Lipid Bilayers on Benzophenone-Modified Substrates", Biomacromolecules, 2001, vol. 2, pp. 70-79.

E. Sackmann, "Supported Membranes: Scientific and Practical Applications", Science, Jan. 5, 1996, vol. 271, pp. 43-48.

S.M. Nielsen et al., "Constitutive Activation of Tethered-Peptide/Corticotropin-Releasing Factor Receptor Chimeras", Proc. Natl. Acad. Sci., Aug. 30, 2000, vol. 97, No. 18, pp. 10277-10281.

S. Angers et al., Detection of β2-Adrenergic Receptor Dimerization in Living Cells Using Bioluminescence Resonance Energy Transfer (BRET), Proc. Natl. Acad. Sci., Mar. 28, 2000, vol. 97, No. 7, pp. 3684-3689.

A.J. Morris et al., "Physiological Regulation of G Protein-Linked Singaling", Physiological Reviews, Oct. 1999, vol. 79, No. 4, pp. 1373-1430.

D.J. Vanderah et al., "Structural Variation in Self-Assembled Monolayers (SAMS) of Omega-Functionalized 1-Thia-oligo(Ethylcne Oxides) [TOEO] Amphiphiles on Gold", Materials Research Society Fall Meeting Abstracts, Boston, p. 518.

Ross et al., "Formation of Self-Assembled, Air-Stable Lipid Bilayer Membranes on Solid Supports", Langmuir 2001, 17 pp. 2305-2307.

* cited by examiner

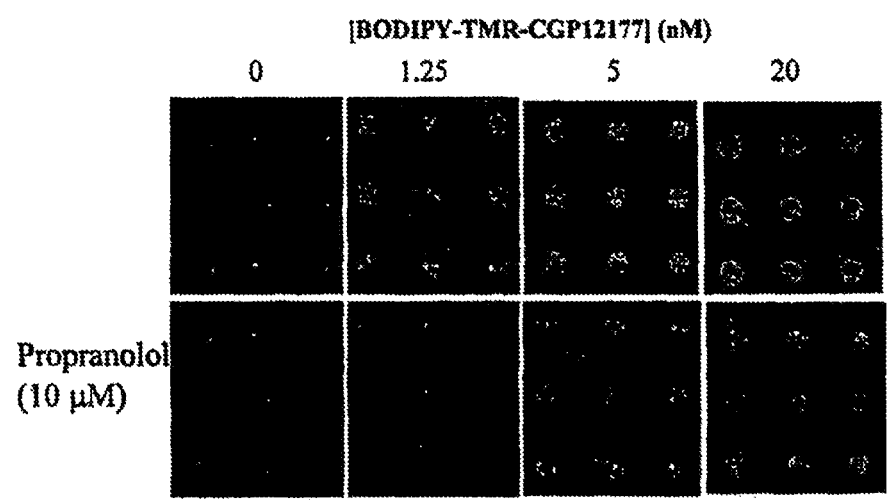

Fig. 10A
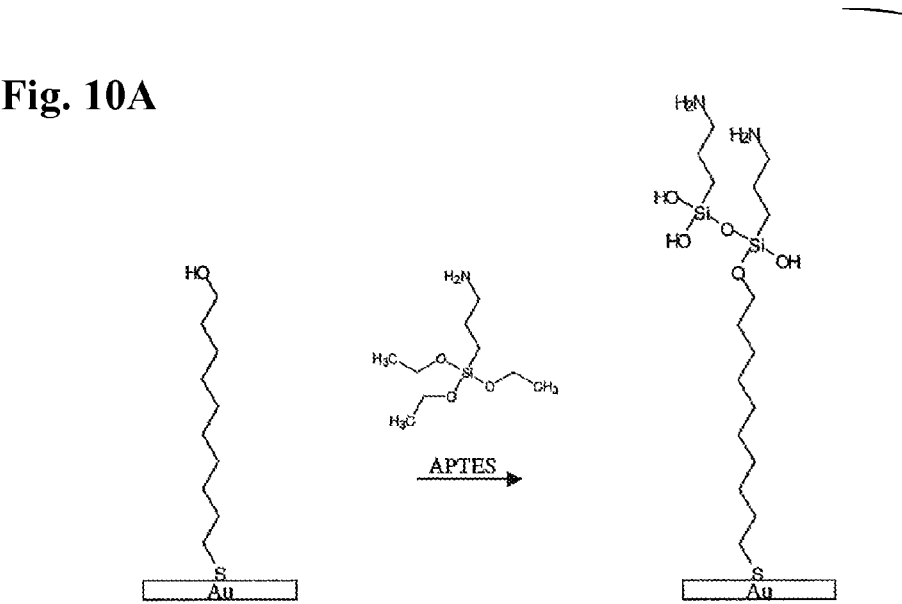
Fig. 10B
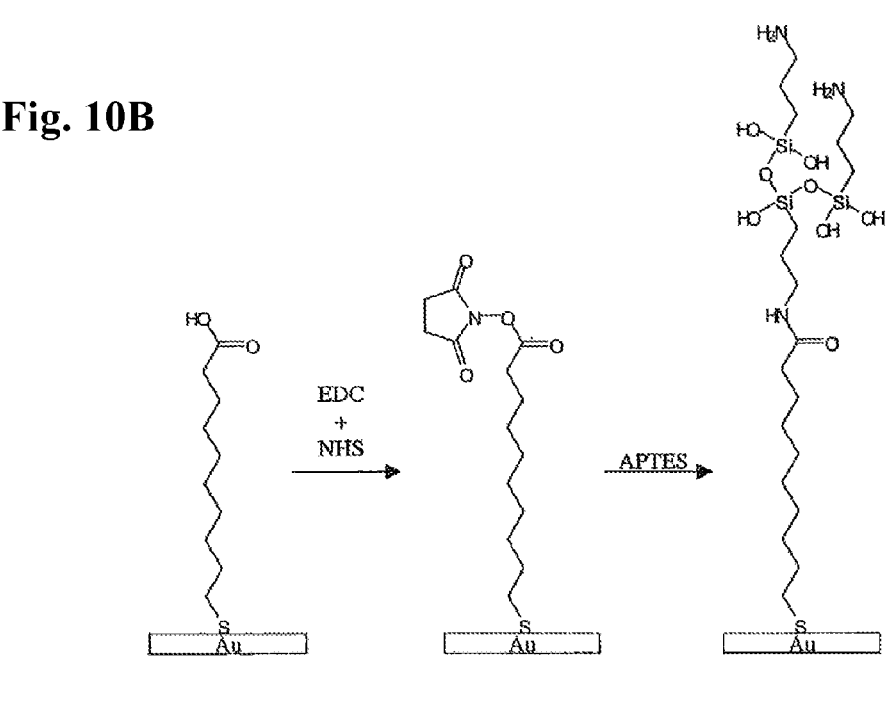
Fig. 10

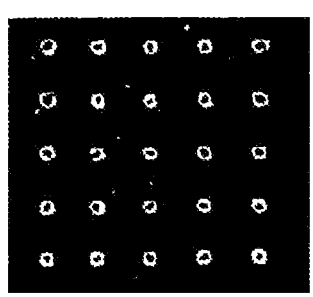 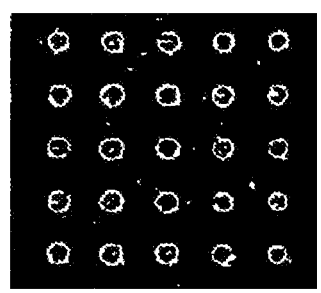 
APTES-MUD  APTES-MUA  CMT-GAPS™
Fig. 11A  Fig. 11B  Fig. 11C
Fig. 11

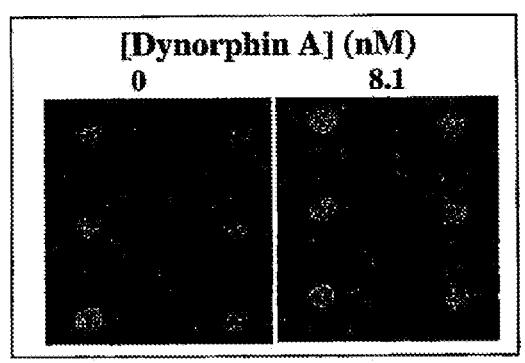
Fig. 14A
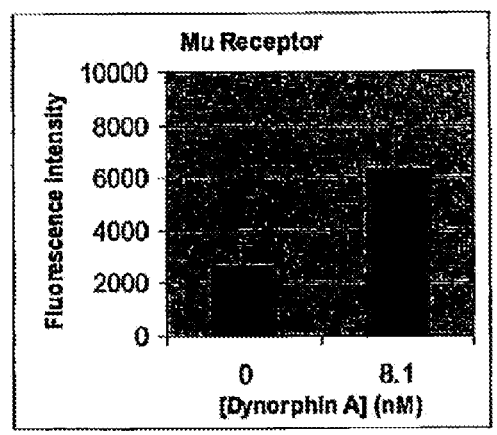
Fig. 14B
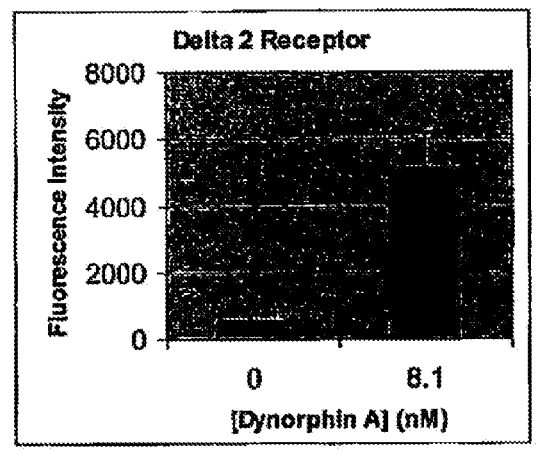
Fig. 14C
Fig. 14

Fig. 15A
Silane Chemistry
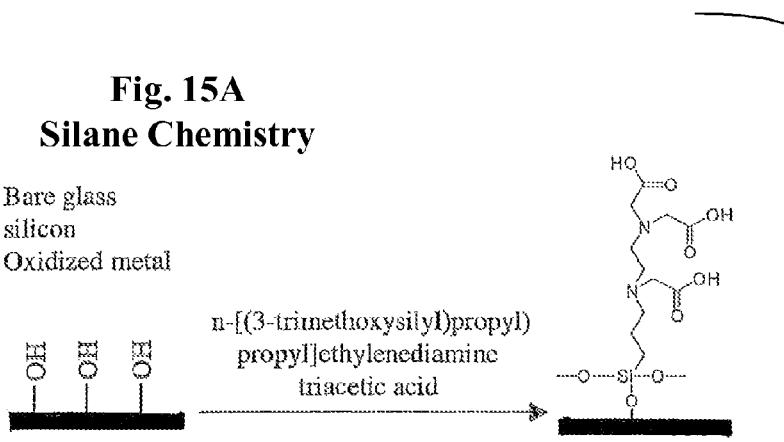
Fig. 15B
Thiol Chemistry
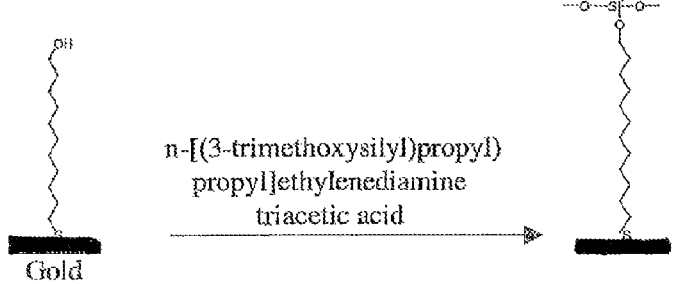
Fig. 15C
Thiol Chemistry
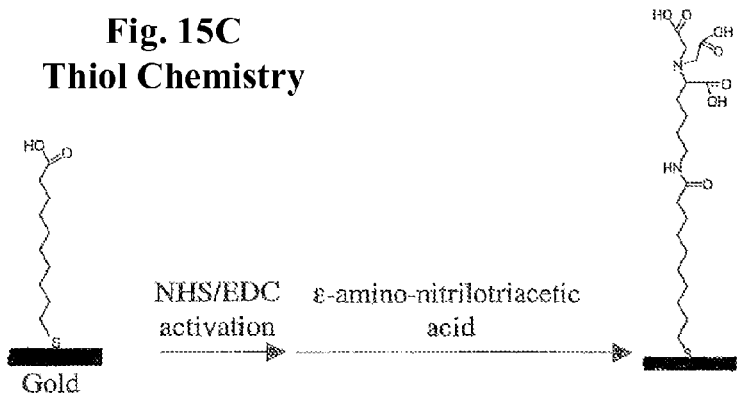
Fig. 15

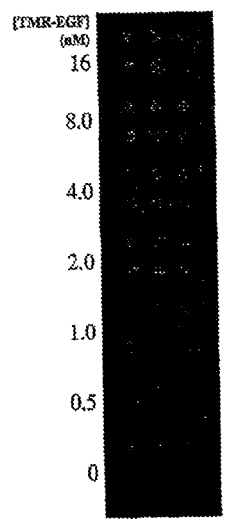
Fig. 16A
Fig. 16B
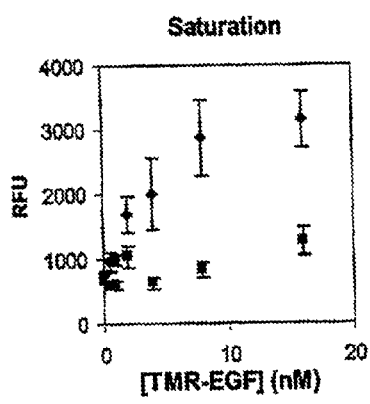
Fig. 16C
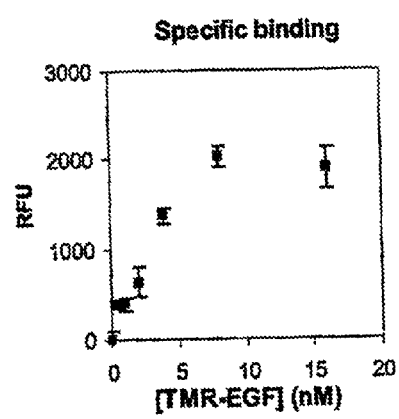
Fig. 16D
Fig. 16

ARRAYS OF BIOLOGICAL MEMBRANES AND METHODS AND USE THEREOF

CROSS-REFERENCE TO RELATED APPLICATION

This Application is a Continuation of U.S. Ser. No. 09/974,415, filed Oct. 9, 2001, now U.S. Pat. No. 7,678,539 now U.S. Publication No. 2002-0094544, which is a continuation-in-part application of Ser. No. 09/854,786, filed May 14, 2001, now U.S. Pat. No. 6,977,155, the contents of which are incorporated herein by reference in its entirety, and priority benefit under 35 U.S.C. §120 is claimed.

BACKGROUND OF THE INVENTION

DNA microarrays have become an extremely important bioanalytical tool (e.g. for analyzing gene expression); protein microarray technology has, however, lagged behind. The fabrication of protein arrays is challenging because of difficulties associated with preserving the folded conformation of proteins in the immobilized state, and high amounts of non-specific binding to immobilized proteins. As a large fraction of drug targets are membrane bound proteins (e.g., G-protein coupled receptors, ion-channels, etc.), there is an impetus to develop tools for high-throughput screening against membrane bound proteins. Membrane proteins maintain their folded conformation when associated with lipids; therefore, to create arrays of such proteins it is important to first develop surfaces that support the binding of membranes. Bilayer-lipid membranes adsorbed onto solid supports, referred to as supported bilayer-lipid membranes, can mimic the structural and functional role of biological membranes. (See Sackmann, E. Science 1996, 271, 43-48; Bieri, C. et al., *Nature Biotech,* 1999, 17, 1105-1108; Groves, J. T. et al., *Science* 1997, 275, 651-653; Lang, H. et al., *Langmuir* 1994, 10, 197-210; Plant, A. L. et al., *Langmuir* 1999, 15, 5128-5135; and Raguse, B. et al., *Langmuir* 1998, 14, 648-659.) These hybrid surfaces were developed to overcome the fragility of black lipid membranes while preserving aspects of lateral fluidity observed in native biological membranes.

Surfaces that bind lipid membranes can be broadly classified into three categories:

(i) hydrophobic surfaces (e.g., self-assembled monolayers presenting terminal methyl groups) that support the adsorption of lipid monolayers; these are of limited utility as they cannot be used to incorporate membrane-spanning proteins (Plant, A. L., *Langmuir* 1999, 15, 5128-5135);

(ii) hydrophilic surfaces (e.g., glass surfaces) that bind bilayer-lipid membranes; these are also of limited utility as they can only be used to incorporate membrane-spanning proteins with extra-membrane domains that are less thick than the layer of adsorbed water (~1 nm) (Groves, J. T. et al., *Science* 1997, 275, 651-653; and Groves, J. T. et al., *Langmuir* 1998, 14, 3347-3350); and (iii) amphiphilic surfaces that contain hydrophobic and hydrophilic portions and bind bilayer-lipid membranes; these offer the potential for incorporating a wide variety of membrane-spanning proteins (Lang, H. et al., *Langmuir* 1994, 10, 197-210; Raguse, B. et al., *Langmuir* 1998, 14, 648-659; and Vanderah, D. J. et al., *Materials Research Society Fall Meeting Abstracts*, Boston, 1999).

Methods to create arrays of membranes would enable high-throughput screening of multiple targets against multiple drug-candidates. Arrays of membranes may be obtained by fabricating grids of titanium oxide on a glass substrate as titanium oxide resists the adsorption of lipids (Boxer, S. G. et al. *Science* 1997, 275, 651-653; and Boxer, S. G. et al. *Langmuir* 1998, 14, 3347-3350). Micropipeting techniques have been used to spatially address each corralled lipid-binding region (Cremer, P. S. et al., *J. Am. Chem. Soc.* 1999, 121, 8130-8131). However, these methods are cumbersome and require the fabrication of patterned surfaces. To make membrane arrays by printing membranes on unpatterned surfaces, it would be necessary to confine the membrane to the printed areas without lateral diffusion of the membrane molecules to the unprinted areas. Boxer et al. have demonstrated that it is possible to pattern lipids on glass surfaces by microcontact printing using poly-dimethylsiloxane (PDMS) stamps "inked" with phosphatidylcholine (PC). They attributed the lateral confinement of the lipids to the stamped regions, to the self-limiting expansion of PC membranes to ~106% of the original printed areas (Hovis, J. et al., *Langmuir* 2000, 16, 894-897). The methods used by Boxer et al., however, have certain limitations. First, Boxer and co-workers carried out the stamping of lipids on surfaces immersed under water (Hovis 2000). Second, lipids adsorbed on the bare-glass substrates used by Boxer and co-workers spontaneously desorbed when drawn through an air-water interface (Cremer 1999). Cremer et al., propose in WO01/20330 the use of spatially addressed lipid bilayer arrays that remain submerged underwater to preserve the planar support structure. Such systems may not be practical for robust, high throughput, microarray based assays.

SUMMARY OF THE INVENTION

The present invention overcomes the problems and disadvantages associated with prior art arrays by providing an array comprising a plurality of biological membrane microspots associated with a surface of a substrate that can be produced, used and stored, not in an aqueous environment, but in an environment exposed to air under ambient or controlled humidities. Preferably, the biological membrane microspots comprise a membrane bound protein. Most preferably, the membrane bound protein is a G-protein coupled receptor (GPCR), a G protein, an ion channel, a receptor serine/threonine kinase, a receptor guanylate cyclase or a receptor tyrosine kinase.

In embodiments in which the biological membrane microspot comprises a GPCR, the GPCR may be oriented depending on the application of the array, such that a desired domain, i.e. extracellular or intracellular, faces the solution. For example, orientation of the GPCR with its extracellular domain facing the solution is preferred for applications related to screening of ligands. The orientation with the intracellular domain facing the solution is preferred for functional arrays. The desired orientation can be accomplished using substrate surface modification techniques discussed in detail below.

In another embodiment, the GPCRs contained within the microspots include members of a single or several related subfamily of GPCRs. These arrays are referred to as "family-specific arrays." Additionally, some GPCRs are found highly expressed in certain tissue types including tumor tissue. This information is used to create arrays of GPCRs having similar tissue distribution (tissue-specific arrays) or similar physiological/pharmacological roles (function-specific arrays).

The substrate for use in the array of the present invention can comprise glass, silicon, metal or polymeric materials. The substrate can be configured as a chip, a slide or a microplate.

In certain embodiments, the surface of the substrate is coated. Preferably, the coating is a material that enhances the affinity of the biological membrane microspot for the substrate. A most preferred coating material confers a contact angle ranging from about 15° to 80°.

The coating material can be a silane, thiol, or a polymer (biological or synthetic). Preferably, when the material is a thiol, the substrate comprises a gold-coated surface. Preferably, the thiol comprises hydrophobic and hydrophilic moieties. Most preferably, the thiol is a thioalkyl compound.

Preferably, when the coating material is a silane, the substrate comprises glass. Preferably, the silane presents terminal moieties including, for example, hydroxyl, carboxyl, phosphate, sulfonate, isocyanato, glycidoxy, thiol, or amino groups. A most preferred silane coating material γ-aminopropylsilane. The coating may form a loosely packed polymer layer referred to as a "polymer cushion".

In an alternative embodiment, the coating material is a derivatized monolayer (or several monolayers), multilayer or polylayer having covalently bonded linker moieties. Most preferably, the monolayer comprises a thioalkyl compound or a silane compound. Preferably, the silane- or thiol-derivatized surface can be further modified with one or more reagents (e.g. cationic polymers such as poly(diallydimethylammonium chloride, or glutaraldehyde) to enable membrane immobilization through non-covalent and covalent bond formation.

Preferably, the thioalkyl compound is selected from the group consisting of a thioalkyl acid, thioalkyl alcohol, thioalkyl amine, and halogen containing thioalkyl compound. Most preferably, the thioalkyl compound is a thioalkyl acid, for example, 16-mercaptohexadecanoic acid.

Preferably, the silane compound is selected from the group consisting of a silyl anhydride, silyl acid, silyl amine, silyl alcohol, silyl thiol, vinyl silane or silyl acrylate.

The bonded linker moiety can comprises a straight or branched $C_{10}$-$C_{25}$ alkyl, alkynyl, alkenyl, aryl, araalkyl, heteroalkyl, heteroalkynyl, heteroalkenyl, heteroaryl, heteroaraalkyl molecule that in turn includes:

(i) a terminal functional group capable of reacting with the derivatized monolayer;
(ii) a hydrophilic spacer region; and
(iii) a hydrophobic membrane adhering region.

Preferably, the terminal functional group is selected from the group consisting of a carboxylic acid, halogen, amine, thiol, alkene, epoxide, acrylate, anhydride, ester, acid halide, isocyanate, hydrazine, maleimide and hydroxyl group. The hydrophilic spacer region preferably comprises n oxyethylene groups, wherein n=2 to 25. The membrane adhering region preferably comprises a straight or branched chain $C_{10}$-$C_{25}$ hydrophobic tail.

In another embodiment, the surface of the substrate comprises gold presenting self-assembled monolayers of alkanethiolates that are derivatized with silanes.

In further alternative embodiments the surface is porous.

The present invention also provides a method for producing an array of biological membranes. One preferred method comprises the steps of providing a substrate having a surface; providing a solution of a biological membrane (as used herein a "solution of a biological membrane" also includes a suspension of a biological membrane); immersing the tip of a pin into the solution; removing the tip from the solution to provide a solution adhered to the tip; contacting the solution with the surface to thereby transfer the solution from the tip to the surface; and repeating the contacting step a plurality of times to provide biological membrane microspots patterned in an array on the surface. Typically, the surface of the substrate is exposed to air under ambient or controlled humidities when the tip of the pin contacts the substrate.

Another preferred method comprises the steps of providing a substrate having a surface; providing a solution of a purified membrane protein; immersing the tip of a pin into the solution; removing the tip from the solution to provide a solution adhered to the tip; contacting the solution with the surface to thereby transfer the solution from the tip to the surface; repeating the contacting step a plurality of times to provide membrane protein microspots patterned in an array on the surface; and incubating the membrane protein microspots with a solution containing naturally occurring or synthetic lipids to re-fold the proteins immobilized on surface into their desired conformations.

A variety of other techniques may also be used to produce the array of biological membranes of the invention. For example, arrays of the present invention can be produced using microstamping (U.S. Pat. No. 5,731,152), microcontact printing using PDMS stamps (Hovis 2000), capillary dispensing devices (U.S. Pat. No. 5,807,522) and micropipetting devices (U.S. Pat. No. 5,601,980).

In a preferred embodiment, the solution comprises a protein. Preferably, the solution comprises a membrane bound protein. Most preferably, the membrane bound protein is a G-protein coupled receptor (GPCR), a G protein, an ion channel or a receptor tyrosine kinase. In certain embodiments, the protein contains a mutation, e.g. a point mutation. In other embodiments, the solution comprises multiple proteins.

In an alternative embodiment, the method includes the additional step of contacting the microspot with a solution comprising a protein.

The present invention further provides for detecting a binding event between a probe array and target compounds. The method comprises contacting a solution comprising the target compound with an array of probe biological membrane microspots associated with a surface of a substrate, and detecting a binding event between at least one or more of the probe microspots with one or more of the constituents of the target. Preferably, at least one of the constituents of the target is labeled and the detection step comprises detecting the presence of the label. The detection of the label is preferably carried out by imaging based on the radioactivity, fluorescence, phosphorescence, chemiluminescence, or resonance light scattering emanating from the bound target. The substrate can be washed to remove unbound target prior to the detection step.

The GPCRs contained within the biological membrane microspots are functional; this functionality can be used to detect a binding event between a probe GPCR and a target compound through the target compound-induced activation of the probe GPCR-associated G protein using, for example, a labeled nonhydrolyzable GTP as the signal probe. Nonhydrolyzable GTP includes, for example, GTPγS.

In an alternative embodiment, the array of microspots is incubated with labeled cognate target and an unlabeled target compound, and the binding event between the unlabeled target compound and the probe is determined by measuring a decrease in the signal of the label due to competition between the cognate labeled target and the unlabeled target compound for the probe. Preferably, the labeled cognate target is incubated with the array before incubation with the unlabeled target. In other embodiments, the target is unlabeled and the binding event is determined by a change in physical properties at the interface or by mass spectroscopy. Preferably, the change in physical properties at the interface is a change in refractive index or electrical impedence.

In an additional embodiment, the invention provides an immobilized membrane comprising a biological membrane associated with a surface of a substrate coated with an amine terminated compound. The substrate can be or comprise glass, metal or plastic. Preferably, the amine terminated compound is a silane. Most preferably, the silane is γ-aminopropylsilane. Alternatively, when the substrate comprises a gold surface, the amine terminated compound molecule can be 11-mercaptoundecylamine. Preferably, the immobilized membrane comprises a membrane bound protein. Most preferably, the membrane bound protein is a G protein coupled receptor, a receptor tyrosine kinase, an ion channel, a receptor serine/threonine kinase, or a receptor guanylate cyclase.

Biosensors and diagnostic devices that comprise the arrays of the invention are also contemplated by the present invention.

DESCRIPTION OF THE DRAWINGS

The file of this patent contains at least one drawing executed in color. Copies of this patent with color drawing(s) will be provided by the Patent and Trademark Office upon request and payment of the necessary fee.

In FIG. 2A the image corresponds to an array that was stored for 7 days at 4° C. in a container saturated with water vapor. In FIG. 2B the images correspond to arrays that were stored for 1, 6, and 14 days in a dessicator at 4° C.

FIG. 3A shows fluorescence images of microarrays of DMPC/DPPC (1:4) lipids doped with FITC-DHPE (2%) on GAPS slides that were subject to repeated immersions in buffer and withdrawn through an air-water interface. (I) Fluorescence image of the lipid array immersed in buffer. (II) Fluorescence image of the array immersed in buffer after being withdrawn five times through an air-water interface. (III) Fluorescence image of the same array immersed in buffer after being withdrawn five more times through an air-water interface. (IV) Fluorescence image of the array in air after drying. (V) Fluorescence image of the same array under buffer after reimmersion. FIG. 3B shows fluorescence images of microarrays of egg PC (1:4) lipids doped with FITC-DHPE (2%) on GAPS slides that were subject to repeated immersions in buffer and withdrawn through an air-water interface, as described above for (I)-(V). The data were collected using a ScanArray 5000 scanner. The buffer used was 50 mM sodium phosphate, pH 7.5.

FIG. 4A shows the fluorescence image of an array incubated with binding buffer only; this image serves as a negative control. FIG. 4B shows the fluorescence image of a second array incubated with a solution of Bodipy-TMR-neurotensin (BT-NT) (2 nM). FIG. 4C shows the fluorescence image of an array incubated with a solution of BT-NT (2 nM) and CGP12177 (1 μM). FIG. 4D shows the fluorescence image of an array incubated with a solution of BT-NT (2 nM) and SCH23390 (1 μM). FIG. 4E shows the fluorescence image of an array incubated with a solution of BT-NT (2 nM) and neurotensin (1 μM). CGP12177 and SCH23390 are ligands that are known not to bind to NTR1 receptors; neurotensin is the cognate ligand for NTR1.

FIG. 5A shows the fluorescence images of 1×5 arrays of microspots of NTR1 incubated in solutions containing different concentrations of BT-neurotensin, as indicated in the figure. FIG. 5B shows fluorescence images of 1×5 arrays of microspots of the galanin receptor incubated in solutions containing different concentrations of cy5-labeled antagonist D, as indicated in the figure. The binding buffer was 50 mM Tris-HCl, 10 mM $MgCl_2$, 2 mM EDTA, 0.1% BSA, at pH 7.4.

FIGS. 8A and 8B show the dose-dependent binding of Bodipy-TMR-CGP12177 (BT-CGP) to human β1 receptor arrays on wheat germ agglutinin (WGA) surfaces in the absence (FIG. 8A) and presence (FIG. 8B) of 10 μM propranolol, a β-receptor antagonist. In both cases, the fluorescence intensity of the β1 receptor arrays increases as the concentration of BT-CGP increases. However, the fluorescence intensities of the β1 arrays in the presence of propranolol are much lower than the corresponding arrays in the absence of propranolol. These results suggest that the binding of BT-CGP to β1 receptor arrays is specific. The fluorescence background on WGA surfaces, due to non-specific binding, is much lower than that on CMT-GAPS surfaces.

FIGS. 10A and 10B are chemical representations of the silane modification of self-assembled monolayers (SAMs) of alkanethiols on gold. SAMs are reacted with 3-aminopropyltrimethoxysilane (APTES) via a one-step (scheme 1—FIG. 10A) or two-step (scheme 2—FIG. 10B) procedure. Alternatively, aminosilanes such as APTES can be electrostatically adsorbed onto alkanethiol SAMs.

FIGS. 11A, 11B and 11C illustrate fluorescence images of GPCR arrays. Arrays of human β-adrenergic receptor subtype 1 (β1) were printed on APTES-modified gold surfaces and incubated with a solution containing BT-CGP 12177. Compared to arrays printed on CMT-GAPS slides, the arrays on gold have ~4× lower background fluorescence.

FIGS. 14A, 14B and 14C show fluorescence images and histogram analysis of arrays of the mu and delta 2 receptors (printed on APTES-modified gold surfaces) in the presence and absence of dynorphin A. Each array has two columns of three replicates of the mu (left column) and delta 2 receptor (right column), respectively. The binding buffer contained 10 mM $MgCl_2$, 100 mM NaCl, 25 nM BODIPY-FL-GTPγS, 0.1% BSA, 3 μM GDP, 50 mM TRIS-HCl, pH 7.4. The incubation time was 90 minutes.

FIGS. 15A, 15B and 15C illustrate chemical modifications of glass or metal surfaces for the oriented immobilization of GPCRs. (15A) Glass surfaces may be derivatized with EDTA-silane, which can be treated with solutions containing nickel ions to form the nickel chelate surface. (15B) The EDTA-silane may be attached to self-assembled monolayers (SAMs) of 11-mercaptoundecanol on gold, or to SAMs of 11-mercaptoundecanoic acid (MUA) via NHS/EDC mediated activation. (15C) Instead of EDTA-silane, e-aminonitrilotriacetic acid groups may be used for coupling to SAMs of MUA (using NHS/EDC).

FIG. 16A shows fluorescence images of seven separate arrays of the epidermal growth factor receptor (EGFR) after incubation with different concentrations of tetramethylrhodamine-epidermal growth factor (TMR-EGF). FIG. 16B shows fluorescence images of seven separate arrays of EGFR after incubation with different concentrations of TMR-EGF in the presence of 500 nM EGF. The EGFR arrays were fabricated on SAMs of 11-mercaptoundecylamine on a gold slide using a quill pin printer. The binding buffer contained 50 mM HEPES-NaOH, 138 mM NaCl, 5 mM KCl, 0.2% BSA. The incubation time was 60 minutes. The fluorescence intensity of the EGFR arrays in the absence and presence of EGF as a function of TMR-EGF concentration is shown in FIG. 16C. The fluorescence intensity of the EGFR arrays due to specific binding is shown in FIG. 16D.

DETAILED DESCRIPTION OF THE INVENTION

Biological membrane arrays, as well as methods for their preparation and use, are provided. In the arrays of the present invention, a plurality of biological membrane probe spots are stably associated with the surface of a solid support. The arrays of the present invention find particular use in identification of ligands for membrane bound proteins, such as G-protein coupled receptors. Additionally, the arrays of the present invention offer tremendous possibilities for high-throughput screening of multiple membrane bound targets against multiple drug-candidates, thereby greatly accelerating the process of drug discovery. In further describing the subject invention, the arrays themselves are first discussed, followed by a description of methods for their preparation. Next, a review of representative applications in which the subject arrays may be employed is provided.

It is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Arrays of the Present Invention

Figure 1:
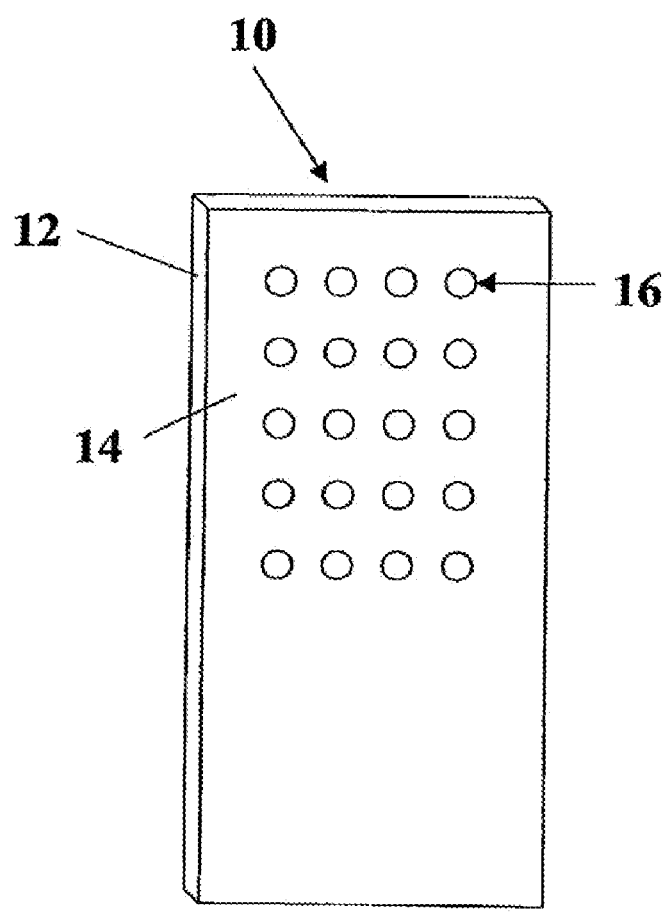
FIG. 1 shows a top view of an array of the present invention.

As illustrated in FIG. 1, the array (10) of the present invention includes a substrate (12) having a surface (14) having a plurality of biological membrane probe microspots (16) covering the surface (14). Each probe microspot on the array comprises a biological membrane of known or unknown composition and, in preferred embodiments, comprises a membrane bound protein. The microspot may comprise multiple different proteins. For example, two different proteins involved in a heterodimer pair can be included in one microspot. The probe microspots on the array may be any convenient shape, but will typically be circular, elliptoid, oval, annular, or some other analogously curved shape, where the shape may, in certain embodiments, be a result of the particular method employed to produce the array. The density of the all of the microspots on the surface of the substrate, i.e. both probe spots and non-probe spots, e.g. calibration spots, control spots, etc., is at least about $1/cm^2$ and usually at least about $10/cm^2$ but does not exceed about $1000/cm^2$, and in many embodiments does not exceed about $500/cm^2$, where in certain preferred embodiments, the density does not exceed about $400/cm^2$, usually does not exceed about $300/cm^2$, and more usually does not exceed about $60/cm^2$. The microspots may be arranged in any convenient pattern across or over the surface of the array, such as in rows and columns so as to form a grid, in a circular pattern, and the like, where generally the pattern of spots will be present in the form of a grid across the surface of the solid support.

In the arrays of the present invention, the microspots are stably associated with the surface of a substrate. By "stably associated" is meant that the microspots maintain their position relative to the substrate under binding and/or washing conditions, e.g., the microspots remain in location and retain biological function when drawn through an air-water interface. As such, the biological membranes which make up the spots can be non-covalently or covalently stably associated with the substrate surface. Examples of non-covalent association include non-specific adsorption, binding based on electrostatic (e.g. ion, ion pair interactions), hydrophobic interactions, hydrogen bonding interactions, surface hydration force and the like, and specific binding based on the specific interaction of an immobilized binding partner and a membrane bound protein. Specific binding-induced immobilization includes, for example, antibody-antigen interaction, generic ligand-receptor binding, lectin-sugar moiety interaction, etc. Examples of covalent binding include covalent bonds formed between the spot biological membranes and a functional group present on the surface of the substrate, e.g. —$NH_2$, where the functional group may be naturally occurring or present as a member of an introduced coating material. In another example, histidine-tagged mutations of GPCRs or membrane proteins can bind to Ni-presenting surfaces through chelating bonds.

Typically, when the biological membrane microspot comprises a membrane bound protein, only one type of protein is included in each microspot of the array. However, in certain situations more than one type of protein is included in each microspot. For example, some GPCRs heterodimerize for their biological functions. (Angers, S. et al., *Proc. Natl. Acad.*

Sci. USA, 2000, 97, 3684-3689.) Additionally, for functional GPCR activity, the biological membrane microspot may include necessary co-effectors and/or adaptors. Furthermore, biological membranes from lysated cells that contain a large number of cell surface molecules can be directly used to fabricate biological membrane arrays.

In a preferred embodiment of the array, the protein included in the microspot differs from the protein included on a second microspot of the same array. In such an embodiment, a plurality of different proteins are present on separate microspots of the array. Typically the array comprises at least about two different proteins. Preferably, the array comprises at least about 10 different proteins. More preferably, the array comprises at least about 50 different proteins. Even more preferably, the array comprises at least about 100 different proteins. Alternative preferred arrays comprise more than about $10^3$ different proteins or more than about $10^4$ different proteins. The array may even optionally comprise more than about $10^5$ different proteins.

In one embodiment of the array, each of the microspots of the array comprises a different protein. For instance, an array comprising about 100 microspots could comprise about 100 different proteins. Likewise, an array of about 10,000 microspots could comprise about 10,000 different proteins. In an alternative embodiment, however, each different protein is included on more than one separate microspot on the array. For instance, each different protein may optionally be present on two to six different microspots. An array of the invention, therefore, may comprise about three-thousand microspots, but only comprise about one thousand different proteins since each different protein is present on three different microspots.

In an alternative embodiment, the array is fabricated using cell membrane preps. Such cell membrane preps contain a large number of different cell surface proteins in addition to the membrane protein of interest. In one example of this embodiment, cell membrane preps obtained from normal and diseased tissues can be used to form an array of the present invention and the resulting array can be used to compare the pharmacological and physiological characteristics of the tissues.

In another alternative embodiment, each of the microspots of the array comprises the same protein of interest but in different amounts, and/or in different embedded environments. For example, the same receptor can be obtained from lysated cell membrane preps, or from purified receptor reconstituted in liposomes or micelles of different compositions. The resulting array can be used to examine the effect of the environment on the stability and functionality of the receptor. hi a further alternative embodiment, each of the microspots of the array comprises the same protein of interest but with different point mutations. The resulting arrays can be used to systematically examine the structure and function relationship of the receptor.

In a further alternative embodiment, the array comprises substantially identical microspots (e.g., microspots comprising the same proteins) or a series of substantially identical microspots that in use are treated with a different analyte (target). For example, an array of the invention can include a "mini array" of 20 microspots, each microspot containing a different membrane bound protein, wherein the mini array is repeated 20 times as part of the larger array.

In another embodiment of the present invention, although the protein of one microspot is different from that of another, the proteins are related. In a preferred embodiment, the two different proteins are members of the same protein family. The different proteins on the invention array may be either functionally related or just suspected of being functionally related. In another embodiment of the invention, however, the function of the immobilized proteins may be unknown. In this case, the different proteins on the different microspots of the array share a similarity in structure or sequence or are simply suspected of sharing a similarity in structure or sequence. Alternatively, the proteins may be fragments of different members of a protein family. In a further embodiment of the invention, the proteins share similarity in pharmacological and physiological distribution or roles.

Substrate

The substrates of the subject arrays comprise at least one surface on which the pattern of probe spots is present, where the surface may be smooth or substantially planar, or have irregularities, such as depressions or elevations. The surface on which the pattern of spots is present may be modified with one or more different layers of compounds that serve to modify the properties of the surface in a desirable manner and will be discussed in more detail below. The surface may also be porous.

The substrate may comprise a ceramic substance, a glass, a metal, a crystalline material, a plastic, a polymer or co-polymer, any combinations thereof, or a coating of one material on another. Such substrates include for example, but are not limited to, (semi) noble metals such as gold or silver; glass materials such as soda-lime glass, pyrex glass, vycor glass, quartz glass; metallic or non-metallic oxides; silicon, monoammonium phosphate, and other such crystalline materials; transition metals; plastics or polymers, including dendritic polymers, such as poly(vinyl chloride), poly(vinyl alcohol), poly(methyl methacrylate), poly(vinyl acetate-maleic anhydride), poly(dimethylsiloxane)monomethacrylate, polystyrenes, polypropylene, polyethyleneimine; copolymers such as poly(vinyl acetate-co-maleic anhydride), poly (styrene-co-maleic anhydride), poly(ethylene-co-acrylic acid) or derivatives of these or the like.

The substrate may take a variety of configurations ranging from simple to complex, depending on the intended use of the array. Thus, the substrate could have an overall slide or plate configuration, such as a rectangular or disc configuration. A standard microplate configuration can be used. In many embodiments, the substrate will have a rectangular cross-sectional shape, having a length of from about 10 mm to 200 mm, usually from about 40 to 150 mm and more usually from about 75 to 125 mm and a width of from about 10 mm to 200 mm, usually from about 20 mm to 120 mm and more usually from about 25 to 80 mm, and a thickness of from about 0.01 mm to 5.0 mm, usually from about 0.1 mm to 2 mm and more usually from about 0.2 to 1 mm.

Coating Material

An array of the present invention may optionally further comprise a coating material on the whole or a portion of the substrate comprising the probe microspots. Preferably the coating material enhances the affinity of the biological membrane microspot for the substrate. Most preferably, the coating material confers a contact angle ranging from about 15° to 80°.

In one embodiment, the coating material is a silane, thiol, disulfide, or a polymer. Preferably, when the material is a thiol, the substrate comprises a gold-coated surface. Preferably, the thiol comprises hydrophobic and hydrophilic moieties. Most preferably, the thiol is a thioalkyl compound.

Preferably, when the coating material is a silane, the substrate comprises glass. Preferably, the silane presents terminal moieties including, for example, hydroxyl, carboxyl, phosphate, glycidoxy, sulfonate, isocyanato, thiol, or amino groups. The coating may form a loosely packed polymer layer referred to as a "polymer cushion". A most preferred silane coating material is γ-aminopropylsilane. γ-aminopropylsilane coated slides (CMT-GAPS™ glass slides) are available commercially from Corning Inc.

In an alternative embodiment, the coating material is a derivatized monolayer or multilayer having covalently bonded linker moieties. The monolayer coating, for example, comprising long chain hydrocarbon moieties, may have for example, but not limited to, thiol (e.g., thioalkyl), disulfide or silane groups that produce a chemical or physicochemical bonding to the substrate. The attachment of the monolayer to the substrate may also be achieved by non-covalent interactions or by covalent reactions.

Preferably, the thiol is a thioalkyl compound and is selected from the group consisting of a thioalkyl acid, thioalkyl alcohol, thioalkyl amine, and halogen containing thioalkyl compound. Most preferably, the thioalkyl compound is a thioalkyl acid, for example, 16-mercaptohexadecanoic acid. Such compounds can be readily synthesized and/or purchased from commercial sources.

After attachment to the substrate the monolayer has at least one reactive functional group. Examples of reactive functional groups on the monolayer coating are, but not limited to, carboxyl, isocyanate, halogen, amine or hydroxyl groups. In one embodiment, these reactive functional groups on the monolayer coating may be activated by standard chemical techniques to corresponding activated functional groups on the monolayer coating (for example, conversion of carboxyl groups to anhydrides or acid halides, etc.). The activated functional groups of the monolayer coating on the substrate may be, but not limited to, anhydrides, N-hydroxysuccinimide esters or other common activated esters or acid halides, for covalent coupling to terminal amino groups of the linker compound. In another embodiment, the activated functional groups on the monolayer coating may be, but not limited to, anhydride derivatives for coupling with a terminal hydroxyl group of the linker compound; hydrazine derivatives for coupling onto oxidized sugar residues of the linker compound; or maleimide derivatives for covalent attachment to thiol groups of the linker compound. To produce a derivatized monolayer coating at least one terminal carboxyl group on the monolayer coating is first activated to an anhydride group and then reacted with a linker compound.

Alternatively, the reactive functional groups on the monolayer coating may be reacted with a linker compound having activated functional groups, for example, but not limited to, N-hydroxysuccinimide esters, acid halides, anhydrides, and isocyonates for covalent coupling to reactive amino groups on the monolayer coating.

The linker compound has one terminal functional group, a spacer region and a membrane adhering region. The terminal functional groups for reacting with the activated functional groups on the activated monolayer coating are for example, but not limited to, halogen, amino, hydroxyl, or thiol groups. Preferably, the terminal functional group is selected from the group consisting of a carboxylic acid, halogen, amine, thiol, alkene, acrylate, anhydride, ester, acid halide, isocyanate, hydrazine, maleimide and hydroxyl group.

The spacer region may consist of, but not limited to, oligo/poly ethers, oligo/poly peptides, oligo/poly amides, oligo/poly amines, oligo/poly esters, oligo/poly saccharides, polyols, multiple charged species or any other combinations thereof. Examples include, but are not limited to, oligomers of ethylene glycols, peptides, glycerol, ethanolamine, serine, inositol, etc., and such that membranes freely adhere to the membrane adhering region of the linker moiety. The spacer region may be hydrophilic in nature. In one preferred embodiment, the spacer has n oxyethylene groups, where n is between 2 and 25. In the most preferred embodiment, the spacer has ten oxyethylene groups. In a preferred embodiment the membrane adhering region or "hydrophobic tail" of the linker compound is hydrophobic or amphiphilic with straight or branched chain alkyl, alkynyl, alkenyl, aryl, araalkyl, heteroalkyl, heteroalkynyl, heteroalkenyl, heteroaryl, or heteroaraalkyl. In a preferred embodiment, the membrane adhering region comprises a $C_{10}$ to $C_{25}$ straight or branched chain alkyl or heteroalkyl hydrophobic tail. In the most preferred embodiment, the hydrophobic tail comprises a $C_{10}$ to $C_{20}$ straight or branched chain alkyl fragment.

In another embodiment, the linker compound has a terminal functional group on one end, a spacer, a linker/membrane adhering region and a hydrophilic group on another end. The hydrophilic group at one end of the linker compound may be a single group or a straight or branched chain of multiple hydrophilic groups. For example, but not limited to, a single hydroxyl group or a chain of multiple ethylene glycol units.

In a further embodiment, the "derivatized monolayer" is a self-assembled monolayer (SAM) of an alkanethiol modified with a silane. Alkanethiols preferably include, for example, 11-mercaptoundecanol (MUD), 11-mercaptoundecanoic acid (MUA), 11-mercaptoundecylamine (MUAM), 16-mercaptohexadecanol, and 16-mercaptohexadecanoic acid. Silanes preferably include silanes with different terminal functional groups as specified earlier, including 3-aminopropyltrimethoxysilane (APTES), 3-mercaptopropyltrimethoxysilane, and 3-isocyanatopropyltriethoxysilane. In this embodiment, the substrate preferably comprises a gold surface. As illustrated in Example 4, the use of a substrate comprising a gold surface results in enhanced signal to background ratios compared to arrays printed on glass substrates. Additionally, gold is a preferred substrate for label-free detection techniques including surface plasma resonance (SPR), matrix assisted laser desorption conization mass spectrometry (MALDI-MS) and electrochemical methods.

Biological Membranes

In accordance with the present invention, a "biological membrane" as referred to in the present invention comprises a membrane which may be synthetic or naturally occurring, for example, but not limited to, vesicles, liposomes, monolayer lipid membranes, bilayer-lipid membranes, membranes incorporated with receptors, whole or part of cell membranes, or liposomes containing re-folded proteins, or detergent micelles containing re-folded proteins, or the like. Membranes suitable for use with the present invention are amphiphilic molecules, for example, but not limited to, phospholipids, sphingomyelins, cholesterol or their derivatives. In a preferred embodiment, the membrane includes a membrane-protein. Such membrane proteins include, for example, integral membrane proteins, peripheral membrane proteins and receptors (e.g., G protein-coupled receptors, ion-channel receptors, tyrosine kinase-linked receptors, receptor tyrosine kinases, cytokine receptors, and receptors with intrinsic enzymatic activity). In another embodiment, the membrane may be bilayer-lipid membranes incorporated with, but not limited to, ionophores (for example, but not limited to, valinomycin, nonactin, methyl monesin, coronands, cryptands or their derivatives), ion-channels (for example, but not limited to, protein ionophores, etc.) or synthetic or naturally occurring analytes, for example, but not limited to, antibody, enzyme, lectin, dye, chelating agent and the like.

Moreover, for GPCR arrays, it is preferable, in certain embodiments, that the receptors immobilized are associated with one or more of their coeffectors such as G-proteins and G protein coupled receptor kinases (GRKs). In a preferred embodiment, cell membrane preps from a cell line co-overexpressing a desired receptor and its coeffectors are used. In another embodiment, a reconstituted receptor in a liposome or micelle is used, in which the receptor is associated with one or more preferred coeffectors in a preferable ratio. The coupling of the receptor with its coeffectors can be carried out before or after the receptor is arrayed. The coeffectors can be either purified natural proteins, recombinant proteins with native sequences, or recombinant proteins with unique combinations of subunits such as mutants and chimeras.

Proteins

The proteins incorporated on the array may be produced by any of the variety of means known to those of ordinary skill in the art. In preparation for incorporation on the arrays of the present invention, the protein may be obtained from natural sources or optionally be overexpressed using recombinant DNA methods. Proteins include, for example, GPCRs (e.g. the aderenergic receptor, angiotensin receptor, cholecystokinin receptor, muscarinic acetylcholine receptor, neurotensin receptor, galanin receptor, dopamine receptor, opioid receptor, erotonin receptor, somatostatin receptor, etc), G proteins, ion-channels (nicotinic acetylcholine receptor, sodium and potassium channels, etc), receptor tyrosine kinases (e.g. epidermal growth factor (EGF) receptor), and other membrane-bound proteins. Mutants or modifications of such proteins may also be used. For example, some GPCRs possessing single or multiple point mutations retain biological functionality and may be involved in disease. (See, Stadel, et al., Trends in Pharmocological Review, 1997, 18, 430-437.)

Additionally, the proteins can also (or independently) be modified to include an agonist (or peptide) attached at the N-terminus. GPCRs modified in such a way can be constitutively activated (Nielsen, S. M. et al., *Proc. Natl. Acad. Sci. USA*, 2000, 97, 10277-10281).

Moreover, for GPCR arrays, it is preferable, in certain embodiments, that the receptors be immobilized in an oriented manner. For example, to improve performance of GPCR arrays for ligand screening, the GPCRs are oriented with their ligand-binding sites (extracellular domains) to the solution and intracellular domain facing the substrate. This can be accomplished by a number of methods. For example, the surface of the substrate is modified to contain nitrilotriacetic acid (NTA) groups or ethylenediamine triacetic acid (EDTA) groups chelated to nickel. This surface can be used for immobilizing recombinant GPCRs with histidine tags at their C-terminus. FIGS. 15A, 15B and 15C illustrate the chemical modification of glass or metal surfaces for the oriented immobilization of GPCRs. Surfaces presenting NTA groups or EDTA groups can be conveniently obtained by silane chemistry on glass or metal oxide surfaces, or via thiol chemistry on gold-coated surfaces. Compounds for these surface chemistries are commercially available (e.g. N-[(3-trimethoxysilyl)propyl)propyl]ethylenediamine triacetic acid; Hüls, Inc.).

In an alternative approach for immobilizing GPCRs with their extracellular domains exposed to solution, anti-G-protein antibodies can be used. This approach has the advantage that the G-proteins do not have to be expressed with histidine-tags.

Alternatively, to improve the performance of GPCR arrays for functional assays, the GPCRs are oriented with their intracellular side facing the solution and extracellular domains facing the substrate. This can be accomplished by a number of methods, including, for example, modifying the substrate surface with lectins such as wheat germ agglutinin (WGA). These surfaces can be used for immobilization of GPCRs through glycosylated moieties in the N-terminal of the receptor, or other cell surface moieties present in the cell membrane.

GPCR Theme Arrays: Selectivity Screening

The selectivity of a potential drug compound to a targeted GPCR versus other GPCRs in the same organ, tissue or even single cell is an extremely important factor to be considered and monitored during drug development. Currently almost all HTS techniques are related to single target screening at one time. GPCR arrays can be used to evaluate the selectivity of multiple compounds of interest to a variety of receptors. In an embodiment of the present invention, the arrays are fabricated GPCR theme arrays, in which the receptors arrayed on the surface include members of a single or several related subfamilies of GPCRs (See Example 3).

Some GPCRs and their mutants are related to the development of certain tumors. For example, some mutations of rhodopsin are related to retinitis pigmentosa, while some mutations of vasopressin V2 are related to X-linked nephrogenic diabetes (Stadel, J. M. et al., Trends in Pharamaco. Sciences 1997, 18, 430-437). Furthermore, some GPCRs are preferably distributed in certain types of tissues. For example, some receptors including the muscarinic acetylcholine receptor, dopamine 2 receptor, histamine 2 receptor, serotonin 4 receptor and prostaglandin receptor prominently distribute in the gastrointestinal system, while some receptors including serotonin 1A/1D and 2A/2C receptor, neurotensin 1 and 2 receptors, opioid receptors (mu, delta, kappa, ORL-1), and dopamine 2/3 receptors prominently distribute in the central nervous system (Stadel, J. M. et al. TIPS 1997, 18, 430-437). Likewise, some receptors are associated with known physiological and pharmacological functions. For example, certain GPCRs for chemokines act as co-factors for HIV infection (Feng, Y. et al., Science 1996, 272, 872-876; Deng, H. K. et al. Nature 1996, 381, 661-666). Additionally, some receptors including serotonin 1A, adenosine A 1/2A and angiotensin receptors play an important role in anxiety and hypertension, while some receptors including opioid receptors, calcitonin gene-related peptide receptors and neuropeptide FF receptors are related to pain control. These properties can be used to fabricate theme arrays of GPCRs having either specific tissue distribution, or specific roles in physiology and pharmacology.

Preparation of the Arrays

The arrays of the present invention are prepared using micro-patterning techniques. Such techniques are well known in the art. In a preferred method of preparation, the tip of a probe (also referred to as a "pin") is immersed into a solution of biological membranes. The tip is removed from the solution to provide solution adhered to the tip. The solution is contacted with the surface of a substrate to thereby transfer the solution from the tip to the surface.

A "pin" as used in the invention may be of any shape, size, and dimension. For example, the pin printing process may involve ring shaped pins, square pins, or point pins, etc. In another embodiment, the direct contact printing may involve single pinprinting or multiple pin printing, i.e. a single pin printing method involving a source plate or multiple pin-printing using a laid out array of multiple pins patterned in any format.

The printing apparatus may include a print head, plate, substrate handling unit, XY or XYZ positioning stage, environmental control, instrument control software, sample tracking software, etc. Such an apparatus includes, for example, a quill pin-printer sold by Cartesian Technologies, Inc.

A typographical probe array having a matrix of probes aligned such that each probe from the matrix fits into a corresponding source well, e.g., a well from a microtiter plate, is preferably used to form a high density array.

A variety of other techniques may also be used to produce the array of biological membranes of the present invention. For example, arrays of the present invention can be produced using microstamping (U.S. Pat. No. 5,731,152), microcontact printing using PDMS stamps (Hovis 2000), capillary dispensing devices (U.S. Pat. No. 5,807,522) and micropipetting devices (U.S. Pat. No. 5,601,980). For radioactive assays using arrays of biological membranes, pippette-based liquid transfer techniques are preferred for fabricating the arrays because such techniques can give rise to spots of larger size with a range of several hundred microns to several mm.

Uses of the Arrays

The present invention also provides for methods of using the biological membrane array. The arrays of the present invention are particularly suited for use in drug development, medical diagnostics, proteomics and biosensors. The sample that is delivered to the array is typically a fluid.

A wide range of detection methods is applicable to the methods of the invention. As desired, detection may be either quantitative, semiquantitative, or qualitative. The invention array can be interfaced with optical detection methods such as absorption in the visible or infrared range, chemiluminescence, and fluorescence (including lifetime, polarization, fluorescence correlation spectroscopy (FCS), and fluorescence-resonance energy transfer (FRET)). Furthermore, other modes of detection such as those based on optical waveguides (PCT Publication WO96/26432 and U.S. Pat. No. 5,677,196), surface plasmon resonance, surface charge sensors, surface force sensors, and MALDI-MS are compatible with many embodiments of the invention.

The assays used on these arrays may be direct, noncompetitive assays or indirect, competitive assays. In the noncompetitive method, the affinity for binding sites on the probe is determined directly. In this method, the proteins in the microspots are directly exposed to the analyte ("the target"). The analyte may be labeled or unlabeled. If the analyte is labeled, the methods of detection would include fluorescence, luminescence, radioactivity, etc. If the analyte is unlabeled, the detection of binding would be based on a change in some physical property at the probe surface. This physical property could be refractive index, or electrical impedance. The detection of binding of unlabeled targets could also be carried out by mass spectroscopy. In the competitive method, binding-site occupancy is determined indirectly. In this method, the proteins of the array are exposed to a solution containing a cognate labeled ligand for the probe array and an unlabled target. The labeled cognate ligand and the unlabled target compete for the binding sites on the probe protein microspots. The affinity of the target for the probe microspot relative to the cognate ligand is determined by the decrease in the amount of binding of the labeled ligand. The detection of binding of the target can also be carried out using sandwich assays, in which after the initial binding, the array is incubated with a second solution containing molecules such as labeled antibodies that have an affinity for the bound target, and the amount of binding of the target is determined based on the amount of binding of the labeled antibodies to the probe-target complex. The detection of binding of the target can be carried out using a displacement assay in which after the initial binding of labeled ligand, the array is incubated with a second solution containing compounds of interest. The binding capability and the amount of binding of the target are determined based on the decrease in number of the pre-bound labeled ligands in the probe arrays.

Another aspect of the invention provides for a method for screening a plurality of proteins for their ability to bind a particular component of a target sample. This method comprises delivering the sample to an array of the invention comprising the proteins to be screened and detecting, either directly or indirectly, for the presence or amount of the particular component retained at each microspot. In a preferred embodiment, the method further comprises the intermediate step of washing the array to remove any unbound or nonspecifically bound components of the sample from the array before the detection step. In another embodiment, the method further comprises the additional step of further characterizing the particular component retained on at least one microspot.

In another embodiment of the invention, a method of assaying for protein-protein binding interactions is provided which comprises the following steps: first, delivering a sample comprising at least one protein to be assayed for binding to the array of the invention; and then detecting, either directly, or indirectly, for the presence or amount of the protein from the sample that is retained at each microspot.

Another embodiment of the invention provides a method of assaying in parallel for the presence of a plurality of analytes in a sample which can react with one or more of the proteins on the array. This method comprises delivering the sample to the array and detecting the interaction of the analyte with the protein at each microspot.

In still another embodiment of the invention, a method of assaying in parallel for the presence of a plurality of analytes in a sample which can bind one or more of the proteins on the array comprises delivering the fluid sample to the array and detecting, either directly or indirectly, for the presence or amount of analyte retained at each microspot. In a preferred embodiment, the method further comprises the step of washing the array to remove any unbound or non-specifically bound components of the sample from the array.

The array may be used in a diagnostic manner when the plurality of analytes being assayed are indicative of a disease condition or the presence of a pathogen in an organism. In such embodiments, the sample which is delivered to the array will then typically be derived from a body fluid or a cellular extract from the organism.

The array may be used for drug screening when a potential drug candidate is screened directly for its ability to bind or otherwise interact with a plurality of proteins on the array. Alternatively, a plurality of potential drug candidates may be screened in parallel for their ability to bind or otherwise interact with one or more proteins on the array. The drug screening process may optionally involve assaying for the interaction, such as binding, of at least one analyte or component of a sample with one or more proteins on an array, both in the presence and absence of the potential drug candidate. This allows for the potential drug candidate to be tested for its ability to act as an inhibitor of the interaction or interactions originally being assayed.

In general, delivery of solutions containing proteins to be bound by the proteins of the array may optionally be preceded, followed, or accompanied by delivery of a blocking solution. A blocking solution contains protein or another moiety which will adhere to sites of non-specific binding on the array. For instance, solutions of bovine serum albumin, milk powder, polyglutamic acid, DNA molecules or lectins may be used as blocking agents.

Functional Assays in GPCR Microarrays

The arrays of the present invention may be used for microarray-based heterogeneous assays to identify the activation and co-effectors of GPCRs. For this use, the assay employs labeled nonhydrolyzable GTP (e.g., radioactive

[$^{35}$S]GTPγS or its fluorescent analogs (e.g. BODIPY-FL-GT-PγS)) to monitor the ligand-stimulated binding of GTPγS to arrays of either i) cell membrane preps containing over-expressed GPCRs and G proteins; or ii) reconstituted vesicles/micelles containing the receptor of interest and its co-effectors. This approach not only enables one to screen agonists against GPCRs in a high throughput manner, but also allows one to identify co-effectors (e.g. coupled Gα protein) of the GPCR.

Upon agonist binding, a GPCR undergoes conformational changes to uncover previously masked G protein-binding sites, thereby promoting interaction with heterotrimeric G proteins. This interaction catalyzes guanine nucleotide exchange, resulting in GTP binding to the a subunit of the G protein. GTP binding leads to dissociation of the $G_\alpha$-GTP complex from the $G_{\beta\gamma}$ subunits. As a consequence of the intrinsic GTPase activity of the $G_\alpha$ subunit, bound GTP is hydrolyzed to GDP, thereby returning the system to its heterotrimeric resting state.

GTPγS is a nonhydrolyzable analog of GTP. The binding of both radioactive and fluorescent GTPγS has been extensively used to measure G protein activation by agonist-bound GPCRs in homogeneous, solution-based assays.

There are diverse groups of G proteins found in tissues and cell types (Morris, C. C. et al.). Gα proteins can be classified into four families ($G_s$, $G_i$, $G_q$ and $G_{12/13}$) based on their biological functions and amino acid homology. Moreover, there are at least five $G_\beta$ and seven $G_\gamma$ proteins reported in the literature. The heterotrimeric G proteins are therefore extremely diverse, taking into account the complexity of the combination of three subunits. It is known that a GPCR couples at least one Gα protein (Morris, C. C. et al.). Furthermore, almost all cell lines preferentially express some rather than all Gα proteins. This raises the complexity of analyzing and normalizing the action of ligands to a GPCR-G protein pathway. For example, if the GPCR co-effectors are absent in a given cell line that is overexpressing the GPCR of interest, the results of ligand screening assays are invalid.

In the absence of ligand-induced activation of the Gα subunit, GTPγS and its analogs bind to members of the Gα proteins with different affinities. For example, BODIPY-FL-GTPγS binds to the unactivated forms of the G proteins $G_o$, $G_s$, $G_{i1}$, and $G_{i2}$ with a $K_d$ of 6, 70, 150 and 300 nM, respectively, in reconstituted vesicle systems (McEwen, D. P., et al.). This gives rise to different basal lines for fluorescence intensity using BODIPY-FL-GTPγS (or radioactivity counts if [$^{35}$S]GTPγS is used). However, the agonist-induced Gα activation greatly promotes the binding of GTPγS.

The present invention provides the following: (1) Use of labeled GTP analogs to screen compounds as agonists or inhibitors for binding to immobilized GPCRs (in planar arrays, or microplate arrays); (2) Fabrication of GPCR arrays using specific biological membranes containing a receptor of interest in the absence and presence of co-effectors; and (3) Use of GPCR microarrays in combination with fluorescent GTPγS to identify the coupled Gα proteins of a GPCR by monitoring the basal line and the percent increase in the signal upon ligand-induced activation of a GPCR and sequential activation of the Gα subunit. Membrane preps from cells co-expressing a GPCR with a $G_{16}$ protein (a universal G protein adapter/co-effector), or lipid vesicles reconstituted with a GPCR and a $G_{16}$ protein can be in the assays of the present invention. Moreover, combinatorial libraries of ligands, generated by phage display techniques, for example, may also be used in the assays of the present invention.

Alternative assays involving β-arrestin or its mutants can also be used to identify the receptors in an array which are activated by agonists. It is reported that there is a two-step mechanism involving the desensitization of GPCRs in living cells (Gurevich et al., 1997; Barak, et al., 1997; Kovoor, et al., 1999). Upon the binding of agonists, the receptor is activated, and then phosphorylated by a G-protein coupled receptor kinase (GRK). Arrestin binds to the activated and phosphorylated receptor, thereby blocking the interaction of the receptor with G proteins. The binding of arrestins to GPCRs requires both the activation and phosphorylation of the GPCRs. However, some of the arrestin mutants, such as the β-arrestin mutants, Arg169Glu and Asp382Ter, are constitutively active, and are able to bind to certain agonist-activated receptors in a phosphorylation-independent manner (Kovoor et al., 1999). Therefore, the biological function of ligands such as natural peptides to the receptors can be measured by monitoring the binding of arrestin or its mutants in the presence or absence of G-protein coupled receptor kinases (GRKs). The arrestin and its mutants can be labeled with isotopes, fluorescence dyes, or biotins. The unlabeled arrestin and its mutants can also be used and examined by label-free detection methods such as surface plasmon resonance. Compared to the GTPγS binding assay that targets receptor-coupled G proteins, the arrestin binding assay is considered to be more straightforward and direct.

Microplate-Based Heterogeneous Assays for GPCR-Ligand Screening

The biological membrane arrays of the present invention can be fabricated using microplates. In order to immobilize receptors on microplate surfaces such that the receptors retain their biological functions, at least the bottom surface of the microplate wells are modified. In certain embodiments it is desirable to modify the surface of the whole well. Depending on the modification, the bottom of the microplate can be either glass, polymer, or gold-based. A number of different surface chemistries can be used for modification, including, for example:

(1). Silanized surfaces. For example, microplates with glass bottoms can be modified using vapor or solution-phase deposition of amine-terminal silanes such as 3-aminopropyltriethoxysilane. Microplates coated with gold can be modified using silanization of SAMs of alkanethiolates. Microplates with polystyrene bottoms can be silanized using vapor or solution-phase deposition after activation of these surfaces with gamma rays, or using cross-linking of silanes to these surfaces.

(2). Wheat germ agglutinin (WGA)-coated surfaces. The coating is normally performed in two steps. The first step involves the silanization of microplates with isocyanatopropylsilane, or the formation and activation of alkanethiolate SAMs on gold microplates. The second step involves the non-covalent or covalent binding of WGA. The WGA-coated surfaces can be used for immobilization of GPCRs through glycosylated moieties in the N-terminal of the receptor.

(3). Antibody-coated surfaces. Anti-GPCR antibodies or anti-G-protein antibodies can also be attached to the bottom of microplates, and used for GPCR immobilization.

To fabricate the microplate arrays of the present invention, small volumes of biological membranes containing a GPCR are delivered to the microplate using, for example, a Cartensian synQuad dispenser. The GPCR microplates of the invention can be used in heterogeneous assays discussed above, including competitive binding assays and functional assays.

In the following, the invention is illustrated by non-limiting examples which describe the invention.

EXAMPLES

Example 1

Materials

Membrane preparations of human β-adrenergic receptor subtype 1 (β1) and dopamine receptor subtype 1 (D1) were purchased from Biosignal Packard (Montréal, Canada). These receptor-associated membranes came suspended in a buffer solution containing 10 mM Tris-HCl, pH 7.4 and 10% glycerol. Human cloned neurotensin receptor subtype 1 (NT1R) and BODIPY-TMR-neurotensin (BT-NT) were purchased from Perkin Elmer Life Science (Boston, Mass.) and were received as membrane associated suspensions in a buffer solution containing 10 mM Tris-HCl (pH 7.4) and 10% sucrose. BODIPY-TMR-CGP12177 (BT-CGP) and BODIPY-FL-SCH23390 (BF-SCH) were purchased from Molecular Probes (Eugene, Oreg.). CGP12177 and SCH23390 were purchased from Tocris Cookson, Inc (Ballwin, Mo.). Neurotensin was purchased from Sigma Chemical Co. (St. Louis, Mo.). Corning CMT-GAPS slides were used as received. The fluorescently labeled ligands and neurotensin were dissolved in DMSO and stored at ~20° C. Before use, the ligand solution was diluted using a binding buffer consisting of 50 mM Tris-HCl, 2 mM EDTA, 1 mM $MgCl_2$, pH 7.4 and 0.1% bovine serum albumin (BSA).

1,2-dilauroyl-sn-glycero-2-phosphocholine (DLPC), L-α-dimyristoylphosphatidylcholine (DMPC), L-α-dipalmitoylphosphatidylcholine (DPPC), and egg phosphatidylcholine (egg PC), were purchased from Avanti Polar Lipids (Alabaster, Ala.). FITC-1,2-dihexadecanoyl-sn-glycero-3-phosphoethanolamine (FITC-DHPE) and Texas Red-1,2-di-hexadecanoyl-sn-glycero-3-phosphoethanolamine (TR-DHPE) were purchased from Molecular Probes Inc.

GPCR and Lipid Printing

Multiple arrays of GPCRs or lipids were printed on each slide (Corning CMT-GAPS slides) using a robotic pin printer (Model PS 5000, Cartesian Technologies Inc.) equipped with quill pins (Telechem). Each 3×3 or 5×5 element array was separated from its neighboring array by at least 6 mm. Membrane preparations containing GPCRs were used for printing as received from the manufacturer without further purification or dilution. After printing the arrays were incubated in a humid chamber at room temperature for one hour, and then used for ligand binding experiments. For longer term storage, the arrays were stored in a dessicator at 4° C.

Ligand Binding

Each array on a given slide was incubated for one hour with 10 μL of a buffered solution (50 mM Tris-HCl, 2 mM EDTA, 1 mM $MgCl_2$, pH 7.4, 0.1% BSA) containing ligand. After incubation, the solutions were carefully removed using a pipette tip attached to a vacuum pump. The slides were rinsed briefly with water and dried under a stream of nitrogen. The slides were imaged in a GenePix 4000A scanner (Axon Instruments, Foster City, Calif.).

Fluorescence Recovery after Photobleaching (FRAP)

Small unilamellar vesicles (SUVs) of 1,2-dilauroyl-sn-glycero-2-phosphocholine (DLPC) mixed with 2% (mol %) Texas Red DHPE were generated by sonicating a suspension of the lipids (1 mg/ml) in buffer; these vesicles were then incubated with the substrate. After extensive and careful washing, supported lipid membranes were formed on these surfaces. FRAP experiments were carried out on these supported lipid membranes on bare glass and GAPS slides using an Olympus AX70 epifluorescence microscope equipped with a CCD detector (Princeton Instruments).

Results and Discussion

Fabrication and Storage of GPCR Arrays

Arrays of GPCRs were fabricated by conventional robotic pin printing, using a quill-pin printer as described in the Experimental Section. Boxer and co-workers have described the importance of transferring membranes onto the solid-support under water; we were, however, concerned that the lipid solution wetted onto the pin would partially dissociate from the pin under water and cause cross-contamination during printing. Moreover, slide racks in commercially available printers are not set up for printing under water. The ability to use off-the-shelf printing equipment for fabricating membrane-protein arrays is an important step toward the widespread fabrication and development of these arrays for bioanalytical applications.

Figure 2:
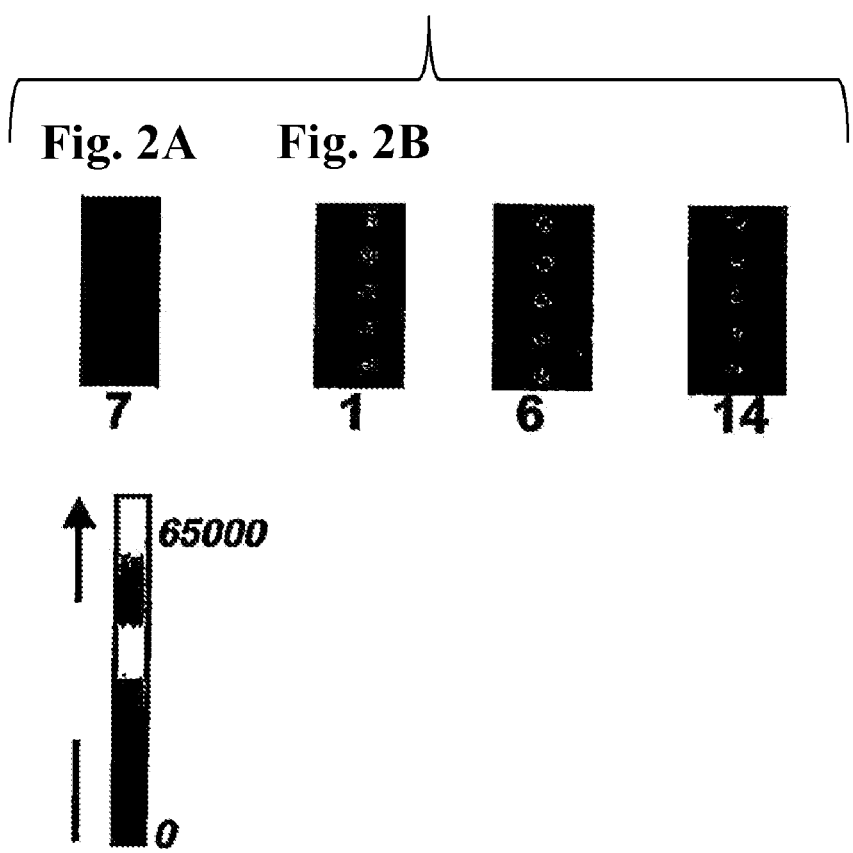
FIGS. 2A and 2B show fluorescence images of 1×5 arrays of microspots of the β-adrenergic receptor (subtype 1) incubated with solutions of BT-TMR CGP12177 (5 nM).

In order to investigate the stability of printed GPCR proteins, arrays of the adrenergic β1 receptor were printed as targets. We first investigated the storage of these arrays under high-humidity at various temperatures (room temp to −80° C.). These high-humidity conditions were chosen because there was a significant body of literature that suggested the importance of an aqueous environment for maintaining the structure of the membrane-protein complex. (Macbeath G., Schreiber, S. L. Science 2000, 289, 1760-1761; Cremer, P. S. Boxer, S. G. J. Phys. Chem. B 1999, 103, 2554-2559). The functional stability of the arrays was evaluated in binding assays using fluorescently labeled cognate ligands and inhibitors using protocols described in Experimental. No ligand binding to the arrays was observed after storage for a week (FIG. 2A). Therefore, we decided to test the stability of these arrays under desiccation. We felt that desiccation would reduce possible protease-induced degradation. Under the new conditions, the slides with printed GPCR arrays were air dried at room temp for a couple of hours, put into slide holders under nitrogen, and stored in desiccators at 4° C. in the dark. Our observations indicate that, over a 2-month period, the adrenergic β1 receptors retained their ligand-binding affinity (FIG. 2B). These stability experiments are a significant feasibility milestone for the manufacture of GPCR arrays.

Mechanical Stability of Membrane Arrays on GAPS Substrates

Figure 3:
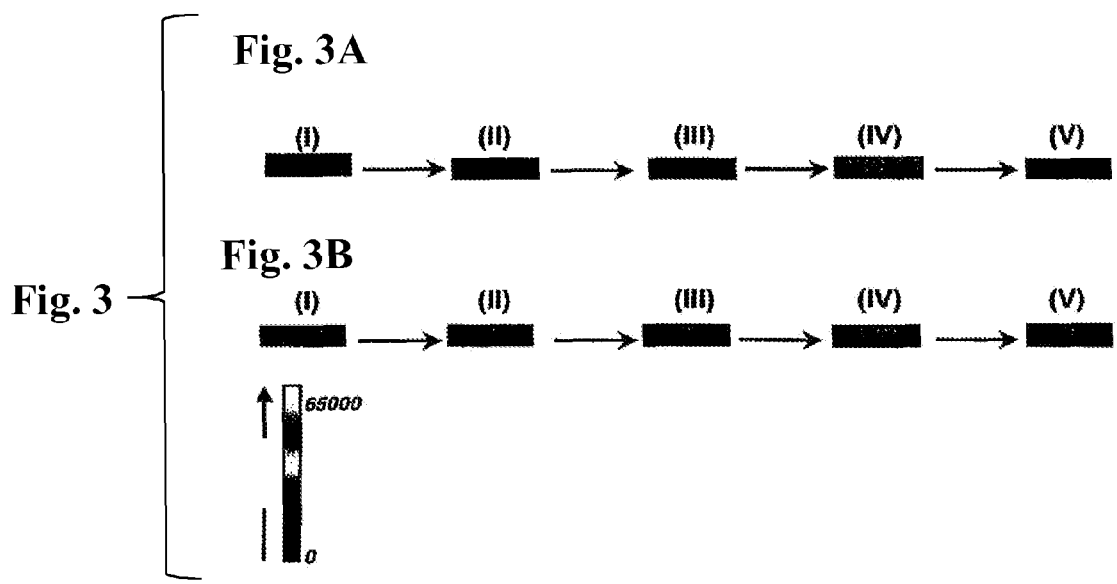
FIGS. 3A and 3B are fluorescence images of microarrays of the present invention.

We were interested in the development of robust binding assays for membrane-protein arrays. Boxer and co-workers have reported that lipids adsorbed onto bare-glass substrates spontaneously desorbed when drawn through an air-water interface (Cremer and Boxer, 1999). We felt that this behavior was a limitation to the use of membrane-protein arrays for bioassays, which often requires protocols in which the slides are withdrawn from solution (e.g. during washes by successive immersions). We therefore investigated surfaces that supported the adsorption of mechanically stable supported membranes; our criterion for stability was that the supported membrane would remain adsorbed when withdrawn through an air-water interface. Among the several surfaces tested, the CMT-GAPS surfaces offered the most stable supported lipids. FIG. 3A shows fluorescence images of arrays of supported membranes consisting of DPPC/DMPC doped with fluorescein-DHPE immersed in buffer that were withdrawn through an air-water interface, immersed in water, dried, and again immersed under water. We did not see any decrease in the fluorescence intensities of these lipid microspots through these successive immersions and withdrawals; these observations indicate that the bound lipids are stable. FIG. 3B shows data on lipids consisting of egg PC; arrays of these lipids are also stable when subject to successive immersions and withdrawals. At room temperature, DMPC/DPPC lipids are in the gel-phase, whereas egg-PC is in the fluid phase. These experiments demonstrate that supported lipid arrays are mechanically robust on GAPS-coated substrates, independent of whether they are in the gel or fluid phase.

We were also interested in determining whether the lipids adsorbed on GAPS substrates had long-range lateral fluidity. This fluidity is an important characteristic of native biological membranes, and is a property that is considered to be physiologically significant (e.g. for processes such as ligand induced receptor dimerization at surfaces, and/or Logan-induced receptor-G protein interactions). Although it is not clear whether this fluidity is required for ligand screening experiments on supported biological membranes, we nevertheless wanted to investigate whether the high mechanical stability of the supported lipids described above necessarily implied that the lipids were not laterally mobile. We made vesicles from fluorescently labeled DLPC lipids and formed supported lipids on the GAPS substrates by vesicle fusion. Using a fluorescence microscope, we observed the fluorescence recovery of a photobleached spot on the supported lipid in a FRAP experiment. A comparative experiment with DLPC vesicles on bare-glass suggested that the recovery was much slower on the GAPS substrate. These experiments suggest there is some lateral fluidity associated with the supported lipids on the GAPS substrates. Our observations on the GAPS substrates are in agreement with the lower and limited mobility of supported membranes on polymer cushions reported by Shen et al (William W Shen, Steven G. Boxer, Wolfgang Knoll, Curtis W. Frank; Biomacromolecules 2001, vol 2, pp 70-79).

Biospecific Binding to GPCR Arrays

Figure 4:
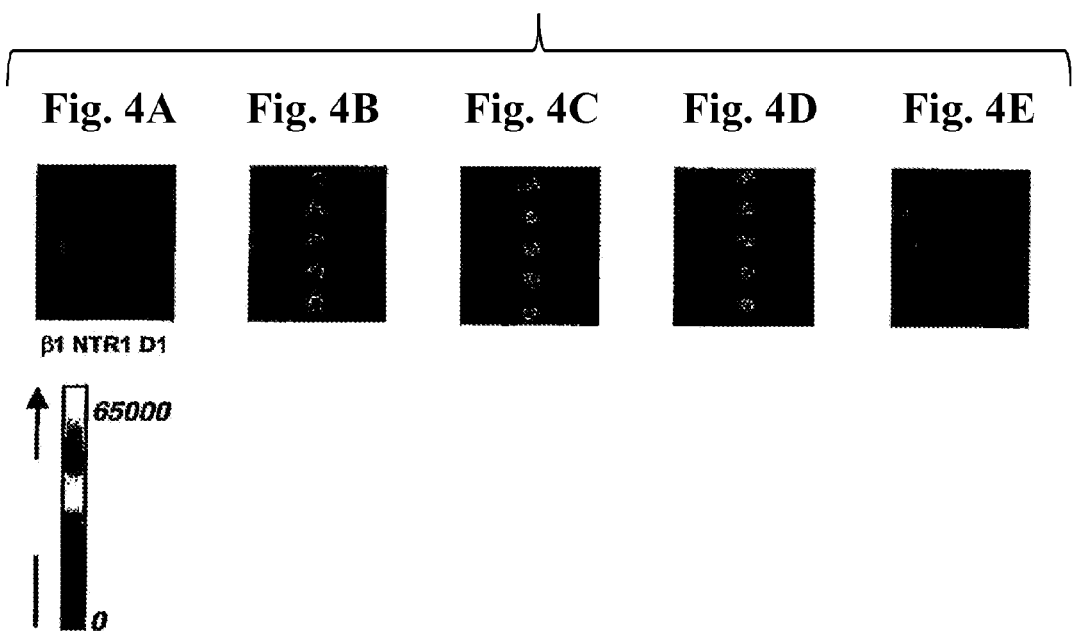
FIGS. 4A-4E show fluorescence images of GPCR arrays, in which each array contains three columns and each column consists of five replicate microspots. Each column of microspots corresponds to a different GPCR. From left to right, these receptors are the β-adrenergic receptor subtype 1 (β1), the neurotensin receptor subtype 1 (NTR1), and the dopamine receptor subtype 1 (D1).

Arrays of GPCRs were fabricated by using a quill-pin printer, as described above. The arrays were then incubated with their fluorescently labeled cognate ligands in direct or competition assays. FIG. 4 shows fluorescence false-color images of five separate arrays printed on a single CMT-GAPS slide; each individual array contains three columns containing 5 replicate spots; each column represents a different GPCR protein. These proteins, from left to right, are the adrenergic receptor ($\beta$1), the neurotensin receptor (NTR1) and the dopamine (D1) receptor, respectively. The first array (FIG. 4A) was incubated with the binding buffer only. As expected, no fluorescence is observed. The second array (FIG. 4B) was incubated with a solution containing fluorescently labeled neurotensin (BT-NT, 2 nM). The image shows that only the array corresponding to NTR1 shows a strong fluorescence signal; this observation suggests that the binding of BT-NT to NTR1 is selective. The specificity of the interaction was further demonstrated by incubating the arrays with solutions containing BT-NT (2 nM) and either CGP12177 (1 $\mu$M) (FIG. 4C), SCH 23390 (1 $\mu$M) (FIG. 4D), or neurotensin (1 $\mu$M) (FIG. 4E). Relative to FIG. 4B, there is no significant decrease in the intensities of spots corresponding to NTR1 in FIG. 4C and 4D. CGP 12177 and SCH 23390 do not bind to NTR1; hence, their addition to the binding solution should not inhibit the interaction of BT-NT with NTR1, in agreement with our observations. Neurotensin is the cognate ligand for NTR1, hence, it competes for binding sites on the NTR1 array. In FIG. 4E, the array was incubated with a solution that contained neurotensin in 500-fold excess over BT-NT; at these ratios, the neurotensin is expected to completely inhibit the binding of BT-NT to NTR1. We do not observe any signal corresponding to the NTR1 array; hence, neurotensin is able to specifically inhibit binding to NTR1. These experiments demonstrate that assays to test the binding of ligands and inhibitors are feasible using GPCR arrays.

Dose Dependent Binding

Figure 5:
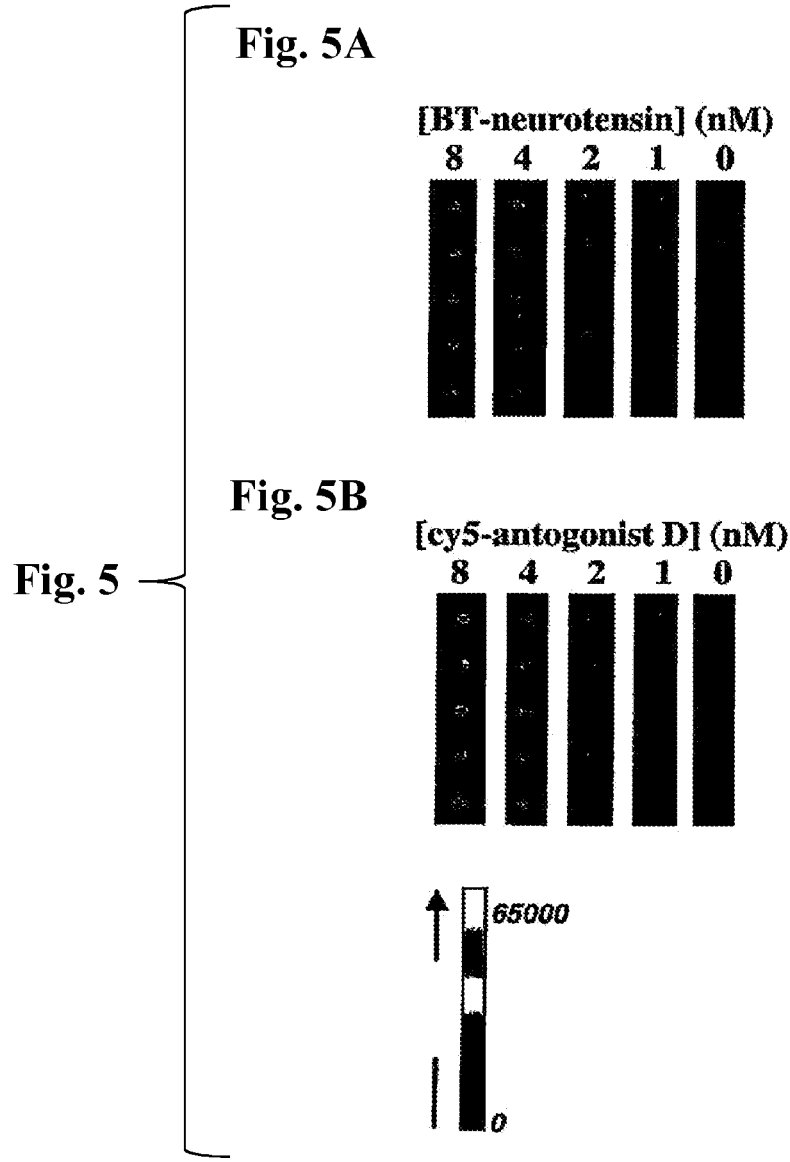
FIGS. 5A and 5B show fluorescence images of arrays of the present invention.

We have investigated the response of the printed GPCR arrays to cognate ligands at different concentrations. FIG. 5A shows fluorescence images of arrays of the neurotensin receptor treated with BT-NT; the data shows that there is an increase in the fluorescence intensity of the arrays when treated with higher concentrations of fluorescently labeled ligand. For the binding of BT-NT to NTR1 arrays, the limit of detection was ~0.1-0.2 nM BT-NT. These results suggest that the dynamic range of GPCR arrays utilizing fluorescently labeled ligands is ~2 logs for this system. FIG. 5B shows data for the binding of cy5-labeled antagonist D to arrays of the galanin receptor; the images show that the fluorescence intensity of the microspots is dependent on the concentration of the ligand.

Figure 6:
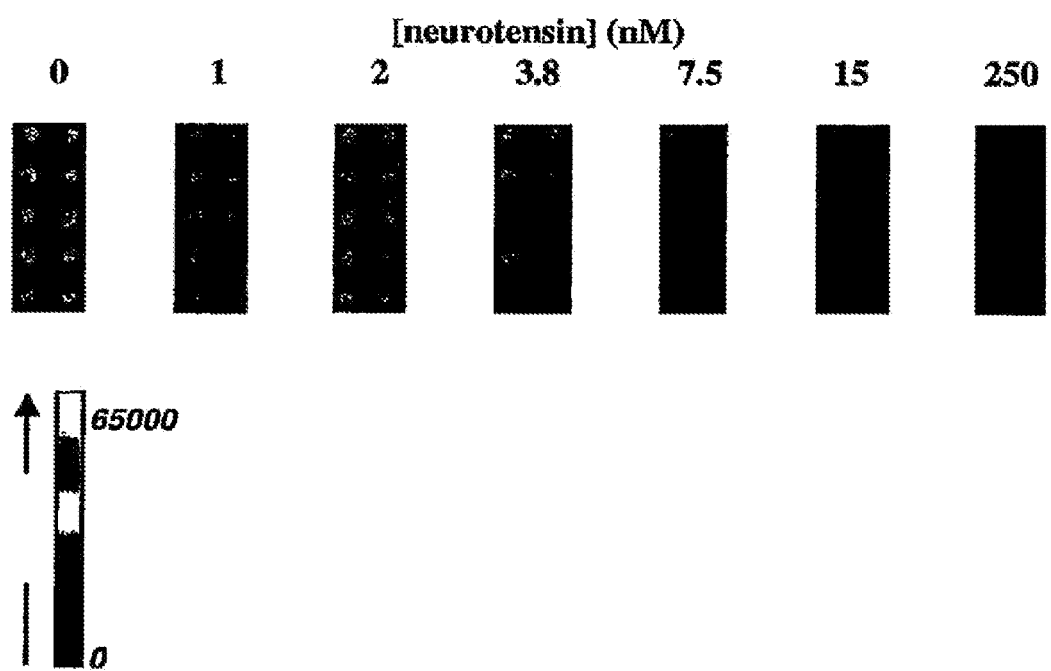
FIG. 6 shows fluorescence images of NTR1 receptor arrays incubated in solutions containing BT-neurotensin at a fixed concentration (1 nM) and unlabeled neurotensin at different concentrations in the binding buffer.
Figure 7:
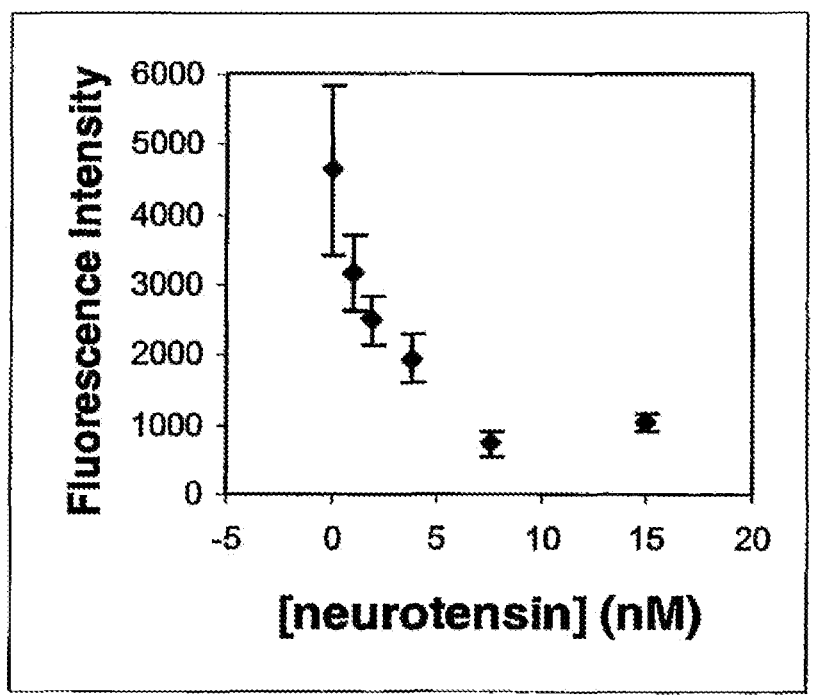
FIG. 7 shows a plot of the fluorescence intensity of NTR1 receptor arrays in the presence of BT-neurotensin as a function of the concentration of neurotensin; statistical data are from the example illustrated in FIG. 6.

The inhibition of binding of the fluorescent ligands to the array is dependent on the relative concentrations of the inhibitor and the labeled ligands, and their respective dissociation ($K_d$). FIG. 6 shows fluorescence images of NTR1 arrays incubated with solutions containing BT-NT (1 nM) and different concentrations of neurotensin (0-250 nM). The data show that there is a decrease in the fluorescence as the concentration of neurotensin is increased. A plot of the fluorescence intensities versus concentration is shown in FIG. 7; based on this plot, we estimate that the inhibition constant ($K_i$) is ~2.5 nM. This value is consistent with the reported value of $K_i$ (2 nM) for neurotensin obtained from fluorescence polarization experiments. These experiments demonstrate that it is possible to obtain estimates of binding constants of ligands and inhibitors using GPCR arrays.

Example 2

Wheat Germ Agglutinin Surface Modification

Glass slides (Corning) were cleaned prior to use by soaking for 30 minutes in piranha etch (7:3 concentrated sulfuric acid: 30% hydrogen peroxide) followed by rinsing with distilled water. The glass slides were soaked in an ethanol solution containing 5% 3-isocyanatopropyltriethoxysilane for an hour, and then rinsed with ethanol and water, and finally dried with a flow of nitrogen. The silanized slides were used immediately for wheat germ agglutinin (WGA) coupling. The coupling was performed by soaking the slides in a solution containing 0.1 mg/ml WGA in 100 mM NaCl, 10 mM phosphate buffer, pH 7.5, followed by rinsing with water and drying. Human $\beta$-adrenergic receptor subtype 1 ($\beta$1) was purchased from Biosignal (Montreal, Canada). The receptor associated membranes were originally suspended in 10 mM Tris-HCl, 5 mM MgCl$_2$ and 10% glycerol, pH7.4, and used directly for printing without further treatment. Eight separate grids of the $\beta$1 receptor were printed on a single WGA surface using a quill pin printer (Model PS5000m Cartesian Technologies Inc.). One hour after printing, each grid was incubated with a different solution that contained varying concentrations of BODIPY-TMR-CGP 12177 in the absence and presence of 10 $\mu$M propranolol. After incubation for 60 minutes the slides were rinsed, dried and imaged in the Cy3 channel of a GenePix scanner. The results are illustrated in FIGS. 8A and 8B.

Example 3

Family-Specific Arrays

Figures 9, 9A, 9B, 9C:
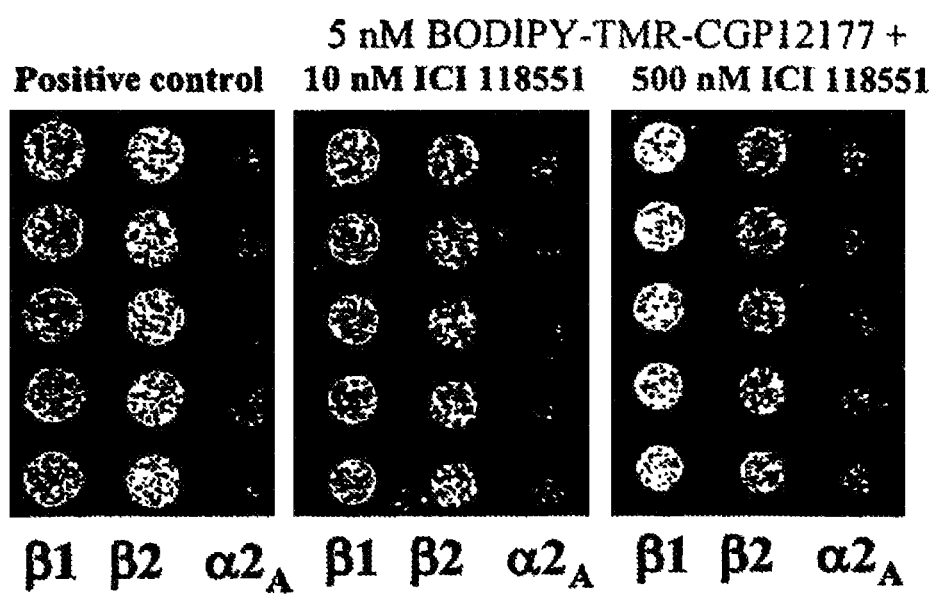
FIGS. 9A, 9B and 9C illustrate GPCR theme arrays used to differentiate the selectivity of compounds of interest to receptors relating to a single subfamily. Multiple arrays of β1, β2 and $α2_A$ were fabricated on an APTES-modified gold surface. Within each array there were three columns of five replicates, corresponding to β1, β2 and $α2_A$ from the left to right column, respectively. The array incubated with 5 nM BT-CGP only was used as positive control (FIG. 9A). The other two arrays were incubated with 5 nM BT-CGP in the presence of different concentrations of ICI 11851: 10 nM ICI 118551 (FIG. 9B) and 500 nM ICI 118551 (FIG. 9C). It is known that the Ki of ICI 118551 is 120 nM for β1, 1.2 nM for β2 and over 10 μM for $α2_A$.

Three receptors belonging to the same family, adrenergic receptors, were arrayed within a single grid, and replicates of this grid were arrayed on a single slide. The receptors were $\beta$1, $\beta$2 and $\alpha$2A, respectively. It has been reported that CGP12177 is a $\beta$1/$\beta$2 antagonist, and a $\beta$3 partial agonist. Arrays were incubated with 5 nM BODIPY-TMR-CGP12177 in the absence and presence of varying concentrations of ICI118551. As illustrated in FIGS. 9A, 9B and 9C, only those spots corresponding to the $\beta$1 and $\beta$2 receptors light up. In the presence of 10 nM ICI118551 (a selective $\beta$2 agonist), the fluorescence intensity of the $\beta$2 receptors decreases, while the intensity of the $\beta$1 receptors remains almost at the same level. However, as the concentration of ICI118551 increases to 500 nM, the fluorescence intensity of $\beta$1 dramatically decreases, while the intensity of $\beta$2 is similar to the intensity observed in the presence of 10 nM ICI118551 These results illustrate that ICI118551 can compete with BODIPY-TMR-CGP12177 binding to both β1 and β2 receptors but with higher affinity to β2, and that the GPCR theme array can be used to differentiate the selectivity of ICI118551 over β1 and β2 receptors.

Example 4

Aminosilanized SAMs of Alkanethiolates on Gold for Immobilization of GPCRs Experimental Details
Preparation of Surfaces Gold-coated microscope slides (10 nM Cr adhesion layer, 100 nm Au) were purchased from Evaporated Metal Films and were cleaned prior to use by soaking for 30 seconds in piranha etch (7:3 concentrated sulfuric acid: 30% hydrogen peroxide) followed by thorough rinsing with distilled water. SAMs of 11-mercaptoundecanoic acid (MUA) or 11-mercaptoundecanol (MUD) were formed by soaking the gold slides in a 1 mM ethanolic solution of the thiol for at least 1 hour. The carboxylic acid groups of the MUA SAMs were converted to active esters by reacting the sample for 30 minutes in a solution containing 75 mM 1-ethyl-3-(3-dimethylaminopropyl)-carbodiimide (EDC) and 15 mM N-hydroxysuccinimide (NHS) in distilled water. This activation step was found to be not necessary, but preferred, for the coupling of aminoterminated silanes. Silanization of SAMs of MUD and NHS-ester modified MUA was accomplished by soaking the slides for one hour in a 5% (v/v) solution of 3-aminopropyltriethoxysilane (APTES) in toluene. The samples were then soaked for five minutes in toluene, rinsed with ethanol, and dried.
GPCR Array Fabrication Arrays of GPCRs were printed on APTES silanized gold surfaces using a Cartesian printer equipped with a quill pin (Telechem). Membrane preparations of human β-adrenergic receptor subtype 1 (β1) were purchased from Biosignal Packard (Montreal, Canada). These receptor-associated membranes come suspended in a buffer solution containing 10 mM Tris-HCl, pH 7.4 and 10% glycerol and were used directly for printing. After printing, the arrays were incubated with a 10 µl solution containing 5 nM BODIPY-tetratmethylrhodamine (BT) labeled CGP 12177 in the absence and presence of 20 µM unlabeled CGP 12177, propranolol, or betaxolol. These reactions were performed in a binding buffer containing 50 mM Tris-HCl (pH 7.4), 10 mM $MgCl_2$, and 0.1% BSA.
Surface Plasmon Resonance Imaging Substrates for SPR imaging were prepared by thermal evaporation of a 1 nm Cr adhesion layer and 45 nm of gold (99.99% gold shot, Kurt J. Lesker Inc.) on SF-10 glass slides (18 mm×18 mm, Schott Glass). Human galanin receptor subtype 1 (NEN Life Sciences) and β-adrenergic receptor subtype 1 were arrayed onto a MUD SAM modified with APTES. The sample was coupled to an SF-10 equilateral prism using index matching fluid (n=1.730, Cargille Labs) and then assembled into an SPRImager instrument (GWC Instruments). In brief, this instrument consists of a collimated white light source, a bandpass interference filter (794 nm±1 nm), a rotation stage, sample mount, flow cell, and an 8-bit CCD camera. The CCD camera lens was replaced with a 6.3× microscope objective (Melles Griot). An initial image of the array was obtained in binding buffer. The array was then exposed to a solution of galanin (5 nM) in binding buffer, allowed to react for 60 minutes, and then washed with buffer. A final image of the array was taken, and a differential SPR image was generated by subtracting the initial SPR image from the final SPR image. Images were analyzed using Scion Image (Scion Image for Windows is a port of the public domain image acquisition and analysis program, NIH Image, developed at the National Institutes of Health; see www.scioncorp.com).
Results and Discussion Two different surface chemistries were developed for the attachment of GPCRs on gold surfaces (see FIGS. 10A and 10B). Scheme 1 (FIG. 10A) utilizes a hydroxyl-terminated SAM of 11-mercaptoundecanol (MUD) as the starting layer that is reacted in one step with 3-aminopropyltrimethoxysilane (APTES). This reaction is analogous to the well known reaction of chloro- and alkoxysilanes with the surface hydroxyl groups of glass and silicon. Silane chemistry has also been used for the modification of SAMs of alkanethiolates. For exampe, Itoh et al. employed alkyltrichlorosilanes to modify SAMs of MUD on copper to enhance the corrosion resistance of the metal. Sun et al demonstrated the vapor-phase reaction of dimethyloctylchlorosilane with hydroxyl and amine-terminated SAMs of thiophenol on gold. Scheme 2 (FIG. 10B) employs a starting layer of 11-mercaptoundecanoic acid (MUA). Prior to reaction with APTES, the carboxylic acid groups of this SAM are first converted into reactive N-hydroxysuccinimide (NHS) esters using 1-ethyl-3-(3-dimethylaminopropyl)-carbodiimide (EDC) and NHS. A network of APTES molecules is covalently anchored to the surface by amide bond formation. For the work described here, preliminary ellipsometric measurements indicate an APTES thickness of ~43 and ~96 on MUD and MUA surfaces, respectively.

In a first experiment, arrays of human β-adrenergic receptor subtype 1 (β1) GPCRs were printed on APTES-modified gold surfaces, incubated with fluorescently labeled CGP 12177, and then imaged using a fluorescence scanner. As seen in FIGS. 11A-11C, both chemistries produce arrays that possess excellent spot morphology and uniformity, and exhibit a high signal to noise ratio. Compared to similar arrays printed on CMT-GAPS slides, these arrays on gold have ~4× lower background fluorescence. This background fluorescence on glass and gold substrates results mainly from small amounts of nonspecifically bound labeled ligands. Because these non-specifically bound ligands are in very close proximity to the gold surface (<~100 Å), fluorescence from the fluorophore is efficiently quenched. At the same time, the fluorescence in each array location is not quenched because the lipid membrane distances the fluorophore at least an additional ~50Å from the gold surface. The fluorescence quenching properties of metals is a well-known phenomenon, and is a sensitive function of the distance between the fluorophore and the metal surface (the amount of quenching has a $(1/r^3)$ distance dependence.) It has been shown that fluorescence quenching by metals is most significant for metal-fluorophore distances <150 Å.

Figure 12:
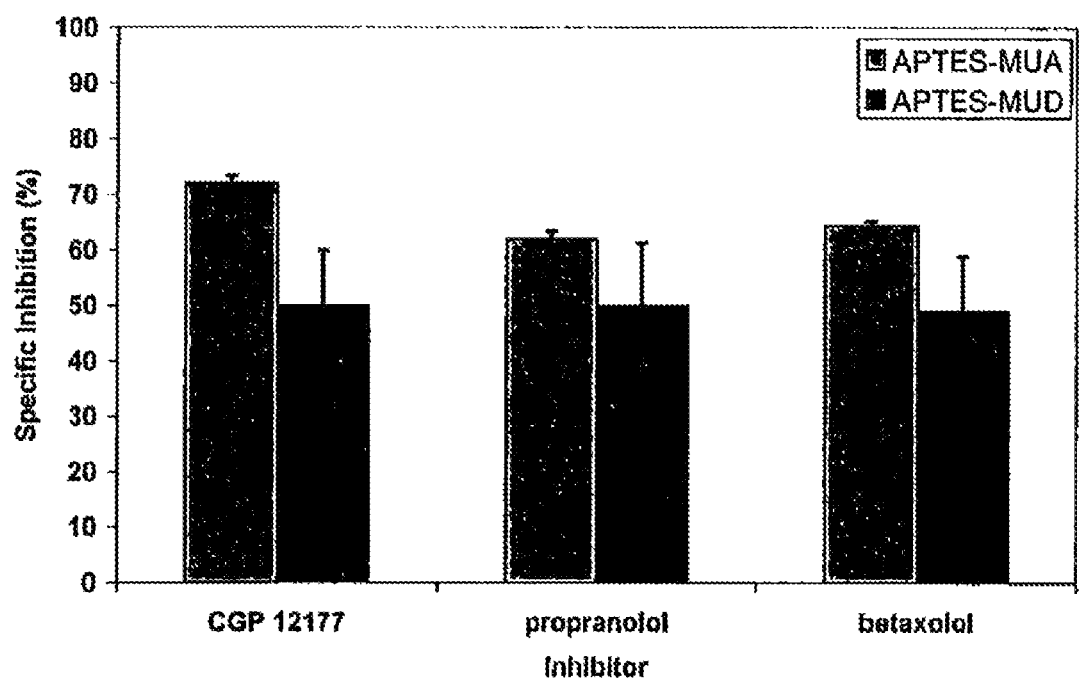
FIG. 12 shows the specific inhibition of the binding of labeled ligand to arrays of β1 adrenergic receptors printed on APTES-modified gold surfaces. The arrays were incubated with solutions containing 5 nM BT-CGP and 20 μM unlabeled inhibitor. The unlabeled inhibitor was CGP12177, propranolol, or betaxolol. Results are the average of two experiments.

To demonstrate that the binding of ligands to arrays of GPCRs on modified gold surfaces is specific, four replicate arrays of the β1 adrenergic receptor were printed on the same slide. One array was incubated with a solution containing labeled CGP 12177 (5 nM). The three remaining arrays were incubated with a solution containing 5 nM labeled CGP 12177 and one of the following unlabeled inhibitors, each at a concentration of 20 µM: CGP 12177, propranolol, betaxolol. For each array, the percent specific inhibition was calculated according to the following formula:

$$\{1-(S_{inhib}/S_{ref})\}\times 100$$

where $S_{inhib}$ is the net fluorescence signal for the arrays co-incubated with labeled CGP and unlabeled ligand, and $S_{ref}$ is the net fluorescence signal for the reference array incubated with labeled CGP only. FIG. 12 shows the results of these experiments performed on APTES attached to SAMs of MUA and MUD. Strong and specific inhibition of the binding of labeled ligand to β1 receptors on both surfaces was observed for all three inhibitors; slightly better inhibition levels were obtained on MUA. Similar levels of inhibition were observed for arrays printed on CMT-GAPS slides (data not shown).

Figures 13, 13A, 13B:
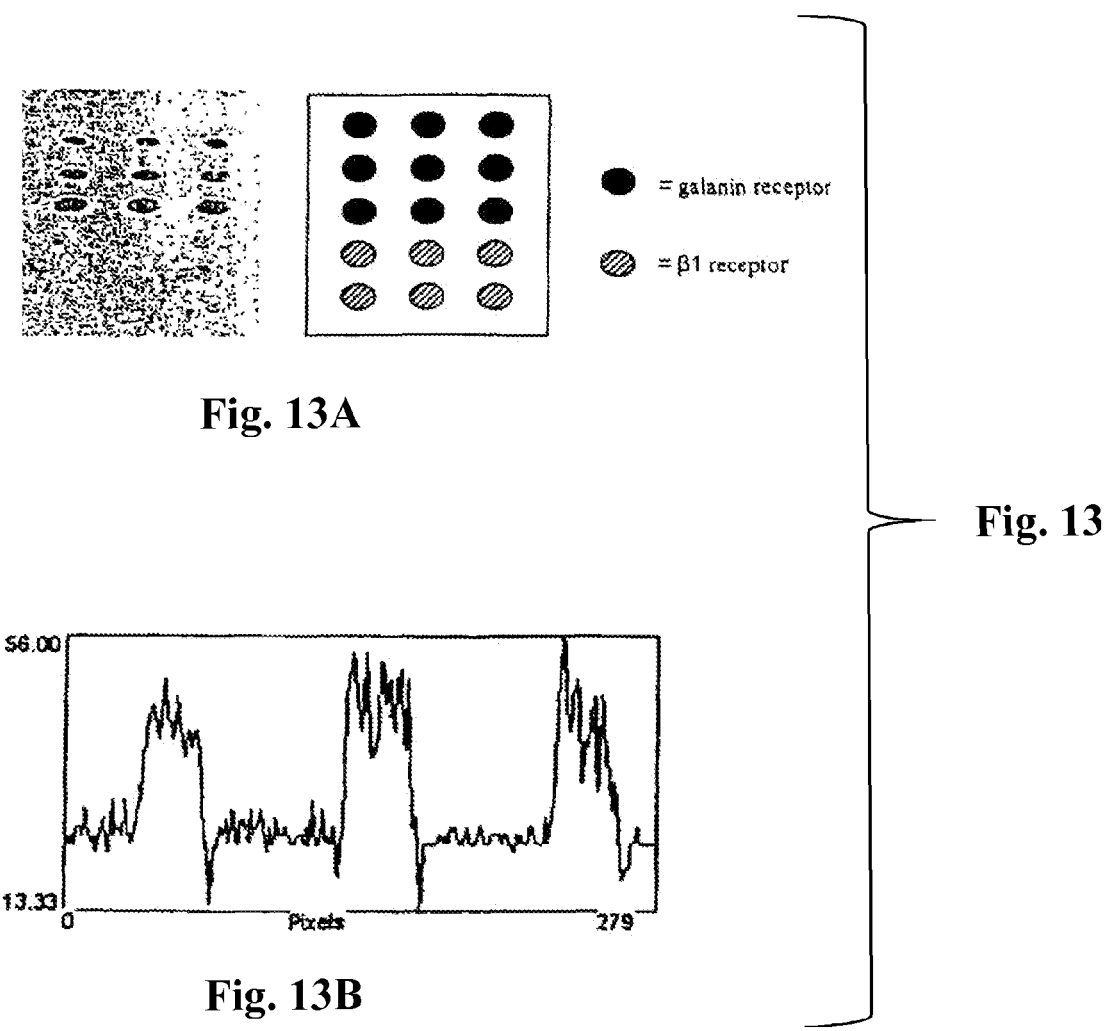
FIGS. 13A and 13B illustrate SPR imaging detection of galanin binding to an array of galanin and β1 adrenergic receptors printed on an APTES-modified gold surface. (A) SPR difference image showing specific binding of galanin to galanin receptor and no binding to the β1 adrenergic receptor. (B) Plot profile showing the binding of galanin to the first row in the array.

SPR Imaging was used to directly detect the specific-binding of unlabeled galanin (3.2 kDa) to arrays of the galanin receptor printed on APTES-modified SAMs of MUD. In this example, a 5×3 array was printed containing 3 rows of the galanin receptor and 2 rows of the β1 adrenergic receptor. After printing, the surface was docked in the SPR imaging instrument and equilibrated with buffer. An initial SPR image of the surface was obtained. Thereafter, a solution of galanin was injected and allowed to incubate with the array for 1 hour. After incubation the array was washed by an injection of buffer. FIG. 13 shows the SPR difference image obtained by subtracting the initial SPR image from the SPR image after the surface was exposed to the solution of galanin. A significant amount of binding was observed for the array locations containing the galanin receptor; in contrast, no binding was detected in array locations containing the β1 adrenergic receptor.

Conclusion

We have developed surface chemistries on gold that allow for immobilization of GPCRs in a biologically active form. The use of a gold substrate results in enhanced signal to background ratios compared to arrays printed on glass substrates. An additional benefit of these surfaces is the possibility of detecting ligand binding in a direct-assay format by label free techniques such as SPR. Although this invention describes the specific use of APTES for immobilization of GPCRs on gold, it is anticipated that the chemical modification of alkanethiols by different silanes is of general utility for the immobilization of a variety of proteins.

Example 5

Functional Assay

Experimental

Human opioid receptor subtypes μ and $\delta_2$ were purchased from Perkin Elmer Life Science (Boston, Mass). The receptor associated membranes were originally suspended in 10 mM Tris-HCl, 5 mM $MgCl_2$ and 10% sucrose, pH7.4, and used directly for printing without further treatment.

Ten separate grids of μ and $\delta_2$ receptors were printed on a single APTES silanized SAM of 11-mercaptoundecanoic acid on a gold slide using a quill pin printer (Model PS 5000, Cartesian Technologies Inc.). Each column in a grid contained five replicates of a single receptor. One hour after printing, each grid was incubated with a different solution that contained varying concentrations of dynorphin A (Sigma Chemical Co., St. Louis, Mo.). These incubations were performed in a buffer containing 50 mM Tris-HCl, 10 mM $MgCl_2$, 0.1% BSA, pH 7.4, 3 μM GDP, 100 mM NaCl, 25 nM BODIPY-FL-GTPγS (Molecular Probes). After incubation for 90 minutes the slides were rinsed, dried and imaged in the FITC channel of a aScanArray 5000 scanner (Packard Instruments).

Results and Discussion

Arrays of the GPCR μ and $\delta_2$-opiod receptors were incubated with solutions containing a fixed (25 nM) concentration of BODIPY-fluorescein labeled GTPγS in the presence and absence of the ligand dynorphin A. FIGS. 14A, 14B and 14C show the results of this experiment. The arrays incubated in the presence of dynorphin A show significantly higher fluorescence. Specifically, the increase in basal level fluorescence was ~2.5 fold for the μ receptor (see FIG. 14B), and ~10 fold for the δ2 receptor (see FIG. 14C). This result suggests that (i) dynorphin A promotes the binding of GTPγS to the Gα proteins present in the cell membrane preps; and (ii) the GPCRs in the array are functional.

Example 6

Epidermal Growth Factor Receptor Microarrays on SAMs of Amino-Terminated Alkanthiolates on Gold Experimental Human epidermal growth factor receptor (EGFR) was purchased from Perkin Elmer Life Science (Boston, Mass.). The receptor membrane preps were from human A431 cells (epithelial tumor cells) that express the EGFR in ~100-fold excess compared to normal epithelial cells. The receptor associated membranes were originally suspended in 50 mM HEPES-KOH, 138 mM NaCl, 5 mM KCl, and 10% sucrose, pH7.7, and were used directly for printing without further treatment. Epidermal growth factor (EGF) and tetramethylrhodamine labeled epidermal growth factor (TM-EGF) were purchased from Molecular Probes (Eugene, Oreg.). The EGF and TM-EGF were reconstituted in distilled water containing 2 mM sodium azide, and divided into single-use aliquots for longer term storage at −80° C.

Fourteen separate grids of the epidermal growth factor receptor were printed on a single gold slide modified with a SAM of 11-mercaptoundecylamine using a quill pin printer (Model PS 5000, Cartesian Technologies Inc.). Each grid contained 2×3 replicates of the receptor. After printing and incubation in a humid chamber for 1 hour, each grid was incubated with a different solution that contained varying concentrations of TMR-EGF in the absence and presence of EGF. These incubations were performed in a buffer containing 50 mM HEPES-NaOH, 138 mM NaCl, 5 mM KCl, 0.2% BSA, pH 7.7. After incubation for 60 minutes the slides were rinsed, dried and imaged in the Cy3 channel of a GenePix scanner.

Results and Discussion

The epidermal growth factor receptor (EGFR) is a 170 kDa membrane-bound glycoprotein and receptor protein tyrosine kinase expressed on the surface of epithelial cells. EGFR is a member of the growth factor receptor family of protein tyrosine kinases, a class of cell cycle regulatory molecules. The receptor undergoes dimerization, conformational changes, and internalization when its ligand (EGF, TGF-α) binds to the extracellular domain. EGF is a 53-amino acid polypeptide hormone that stimulates division of epidermal and other cells.

Arrays of the EGF receptor were incubated with solutions containing an increasing concentration of TMR-EGF in the absence (FIG. 16A) and presence (FIG. 16B) of EGF (500 nM). FIG. 16C shows plots of the average fluorescence intensity of these EGFR arrays as a function of the concentration of TMR-EGF in the absence (diamonds) and presence (squares) of EGF. The amount of signal observed in the presence of 500 mM EGF is small, indicating that the non-specific binding of TMR-EGF is quite low. The specific binding of TMR-EGF to the array exhibits a typical saturation curve response, as shown in FIG. 16D. These results suggest that (i) the binding of TMR-EGF to EGFRs in the arrays is specific with high affinity; and (ii) the EGFRs in the array are functional.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

The references cited throughout the specification including those set forth below are incorporated herein by reference.
1. Morris, A. J. and Malbon, C. C. (1999). "Physiological regulation of G protein-linked signaling." *Physiol. Rev.* 79, 1373-1430.
2. Drews, J. (2000). "Drug discovery: a historical perspective". *Science* 287, 1960-1963.
3. Howard, A. D., McAllister, G., Feighner, S. D., Liu, Q., Nargund, R. P., Van der Ploeg, L. H. T. and Patchett, A. A. (2001) "Orphan G-protein coupled receptors and natural ligand discovery". *Trends in Pharmaco. Sci.* 22, 132-140.
4. Stadel, J. M., Wilson, S. and Bergsma, D. J. (1997). "Orphan G protein-coupled receptors: a neglected opportunity for pioneer drug discovery." *TiPS* 18, 430-437.
5. Civelli, O., Reinscheid, R. K., Nothacker, H.-P. (1999). "Orphan receptors, novel neuropeptides and reverse pharmaceutical research". *Brain Res.* 848, 63-65.
6. Gurevich, V. V., Pals-Rylaarsdam, R., Benovic, J. L., Hosey, M. M. and Onorato, J. J. (1997). "Agonist-receptor-arrestin, an alternative ternary complex with high agonist affinity." *J. Biol. Chem.* 272, 28849.
7. Oakley, R. H., Laporte, S. A., Holt, J. A., Caron, M. G., Barak, L. S. (2000) "Differential affinities of visual arrestin, β-arrestin1, and β-arrestin2 for G protein-coupled receptors delineate two major classes of receptors." *J. Biol. Chem.* 275, 17201-17210.
8. Barak, L. S., Ferguson, S. S. G., Zhang, J. and Caron, M. G. (1997). "A β-arrestin/green fluorescent protein biosensor for detecting G protein-coupled receptor activation.' *J. Biol. Chem.* 272, 27497-27500.
9. Kovoor, A., Celver, J., Abdryashitov, R., Chavkin, C., Gurevich, V. V. (1999). "Targeted construction of phosphorylation-independent β-arrestin mutants with constitutive activity in cells." *J. Biol. Chem.* 274, 6831-6834.
10. Lahiri, J., Kalal, P., Frutos, A. G., Jonas, S. J. and Schaeffler, R. (2000). "Method for fabricating supported bilayer lipid membranes on gold". *Langmuir* 16, 7805-7812.
11. McEwen, D. P., Gee, K. R., Kang, H. C., and Neubig, R. R. (2001). "Fluorescent BODIPY-GTP analogs: real-time measurement of nucleotide binding to G proteins". Anal. Biochem, 291, 109-117.
12. Itoh, M, Nishihara, N, Aramaki, K. (1995). "Preparation and evaluation of two-dimensional polymer films by chemical modification of an alkanethiol self-assembled monolayer for protection of copper against corrosion". J. Electrochem. Soc. 142, 3696-3704.
13. Sun, L., Thomas, R. C., Crooks, R. M., Ricco, A. J. (1991) "Real-time analysis of chemical reactions occurring at a surface-confined organic monolayer". *J. Am. Chem. Soc.,* 113, 8550-8552.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. An array comprising a plurality of biological membrane microspots comprising a G-protein coupled receptor associated with a substrate, wherein the biological membrane is immobilized on an amine terminated silane surface of the formula gamma-aminopropyl silane, the array is stable in air at ambient temperature and ambient humidity, and the array has a microspot density on the surface of the substrate of from about $5/cm^2$ to about $1,000/cm^2$.

2. The array of claim 1, wherein the substrate comprises glass, metal, or plastic.

3. The array of claim 2, wherein the substrate is flat, porous, or nano-porous.

4. The array of claim 1, wherein the amine terminated silane surface has a contact angle of from about 15 to about 80 degrees.

5. The array of claim 1, wherein the amine terminated silane surface enhances the storage stability, assay stability, or mechanical stability of the biological membrane microspots on the substrate.

6. An array comprising a plurality of biological membrane microspots comprising a G-protein coupled receptor associated with a substrate, wherein the biological membrane microspots are immobilized on an amine terminated silane surface and the array is stable when stored under desiccation wherein the silane is gamma-aminopropyl silane.

7. An array comprising a plurality of biological membrane microspots comprising a G-protein coupled receptor associated with a substrate, wherein the biological membrane microspots are immobilized on an amine terminated silane surface and the plurality of biological membrane microspots are air stable on the substrate at ambient humidity wherein the silane is gamma-aminopropyl silane.

8. The array of claim 6, wherein the array has a microspot density on the surface of the substrate of from about $5/cm^2$ to about $1,000/cm^2$.

9. The array according to claim 7, wherein the array has a microspot density on the surface of the substrate of from about $5/cm^2$ to about $1,000/cm^2$.

* * * * *